(12) United States Patent
Nishigaki et al.

(10) Patent No.: US 10,533,934 B2
(45) Date of Patent: Jan. 14, 2020

(54) PARTICLE INSPECTION SYSTEM AND DRIVING METHOD EMPLOYED THEREIN

(71) Applicant: KABUSHIKI KAISHA TOSHIBA, Minato-ku, Tokyo (JP)

(72) Inventors: Michihiko Nishigaki, Kawasaki Kanagawa (JP); Hiroshi Hamasaki, Hiratsuka Kanagawa (JP); Naofumi Nakamura, Tokyo (JP); Kentaro Kobayashi, Tokyo (JP); Hiroko Miki, Kawasaki Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 58 days.

(21) Appl. No.: 15/408,702

(22) Filed: Jan. 18, 2017

(65) Prior Publication Data

US 2017/0122859 A1 May 4, 2017

Related U.S. Application Data

(63) Continuation of application No. PCT/JP2015/057606, filed on Mar. 10, 2015.

(30) Foreign Application Priority Data

Jul. 18, 2014 (JP) .................. 2014-147614

(51) Int. Cl.
*G01N 15/10* (2006.01)
*G01N 15/12* (2006.01)

(52) U.S. Cl.
CPC ..... *G01N 15/1056* (2013.01); *G01N 15/1031* (2013.01); *G01N 15/1209* (2013.01); *G01N 2015/1254* (2013.01)

(58) Field of Classification Search
CPC .......... G01N 15/1031; G01N 15/1209; G01N 15/1056
See application file for complete search history.

(56) References Cited

U.S. PATENT DOCUMENTS 4,891,575 A    1/1990  Kogo et al.
2001/0032495 A1* 10/2001 Ueno ................. G01N 15/1227
                                                    73/61.71
(Continued)

FOREIGN PATENT DOCUMENTS

CN         1678398 A      10/2005
CN       103718029 A       4/2014
(Continued)

OTHER PUBLICATIONS

International Search Report (ISR) and Written Opinion dated May 12, 2015 issued in International Application No. PCT/JP2015/057606.

(Continued)

*Primary Examiner* — Patrick Assouad
*Assistant Examiner* — Feba Pothen
(74) *Attorney, Agent, or Firm* — Holtz, Holtz & Volek PC

(57) ABSTRACT

According to one embodiment, a particle inspection system includes a voltage driving circuit which applies a driving voltage for a particle inspection to a particle inspection chip, a current-voltage conversion circuit which converts, into a voltage signal, a current signal output from the particle inspection chip when the driving voltage is applied to the particle inspection chip, a detection circuit which detects, based on the voltage signal, whether the sample liquid is introduced into a detection region of the particle inspection chip, and an analysis circuit which analyzes the fine particle, in the sample liquid based on the voltage signal. The voltage (Continued)

driving circuit varies the driving voltage based on the detection result of the detection circuit.

18 Claims, 27 Drawing Sheets

(56) References Cited

U.S. PATENT DOCUMENTS

| | | |
|---|---|---|
| 2004/0051154 A1 | 3/2004 | Yamakawa et al. |
| 2004/0178066 A1 | 9/2004 | Miyazaki et al. |
| 2006/0073489 A1 | 4/2006 | Li et al. |
| 2011/0133255 A1 | 6/2011 | Merz |
| 2013/0015066 A1 | 1/2013 | Van |
| 2013/0095510 A1* | 4/2013 | Malecha ............ G01N 27/3273 435/14 |
| 2014/0158540 A1 | 6/2014 | Ohura |
| 2014/0252505 A1 | 9/2014 | Kobayashi et al. |
| 2014/0255911 A1 | 9/2014 | Hongo et al. |
| 2014/0256028 A1 | 9/2014 | Kobayashi et al. |
| 2014/0256031 A1 | 9/2014 | Kobayashi et al. |
| 2015/0041316 A1 | 2/2015 | Miki et al. |
| 2016/0054312 A1* | 2/2016 | Goldsmith ......... G01N 27/4145 506/39 |

FOREIGN PATENT DOCUMENTS

| | | |
|---|---|---|
| JP | 2004132981 A | 4/2004 |
| JP | 2008039541 A | 2/2008 |
| TW | 201011290 A1 | 3/2010 |
| TW | 201140023 A1 | 11/2011 |

OTHER PUBLICATIONS

Taiwanese Office Action dated Mar. 16, 2016 issued in counterpart Taiwanese Application No. 104107572.

\* cited by examiner

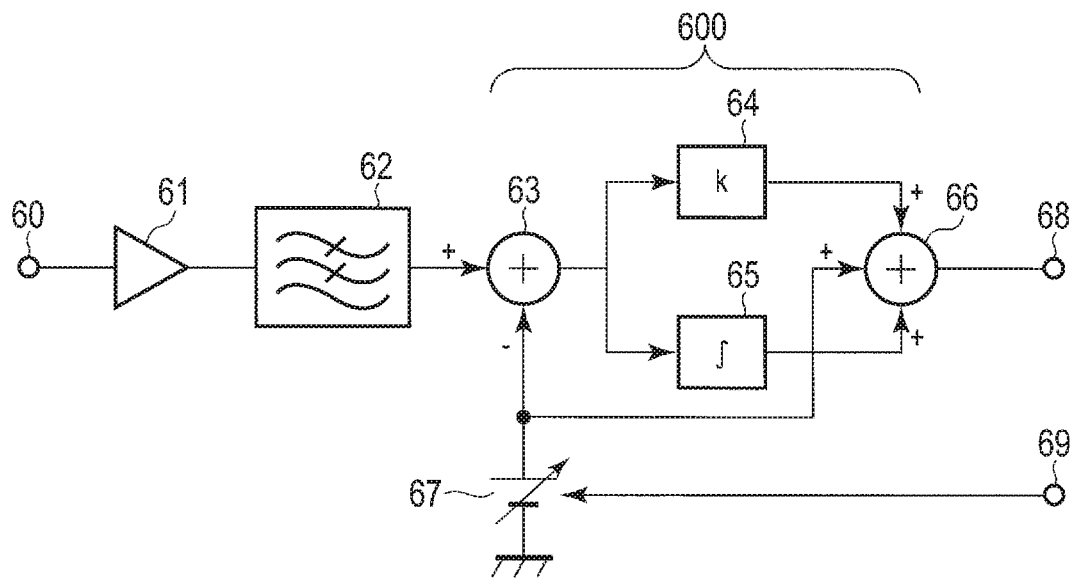
F I G. 11
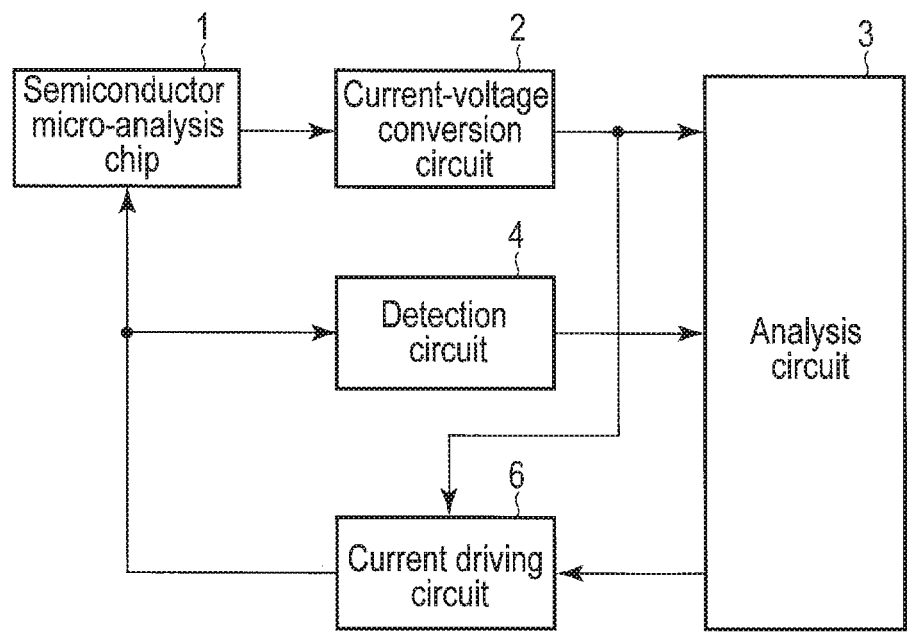
F I G. 12

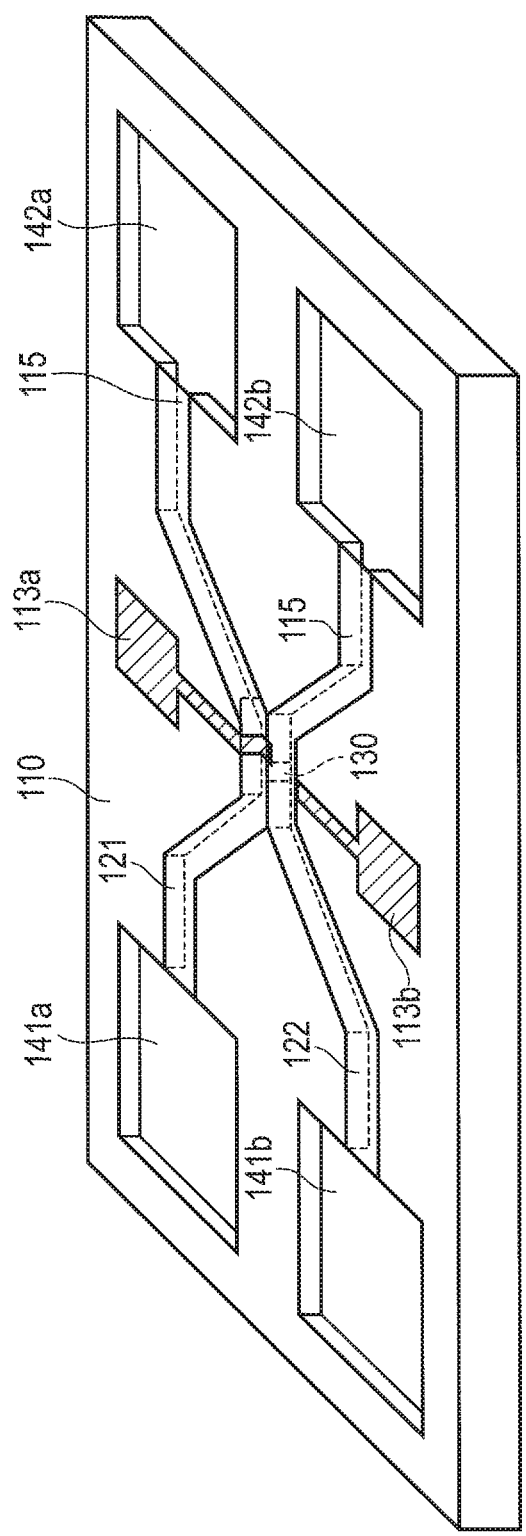
F I G. 17

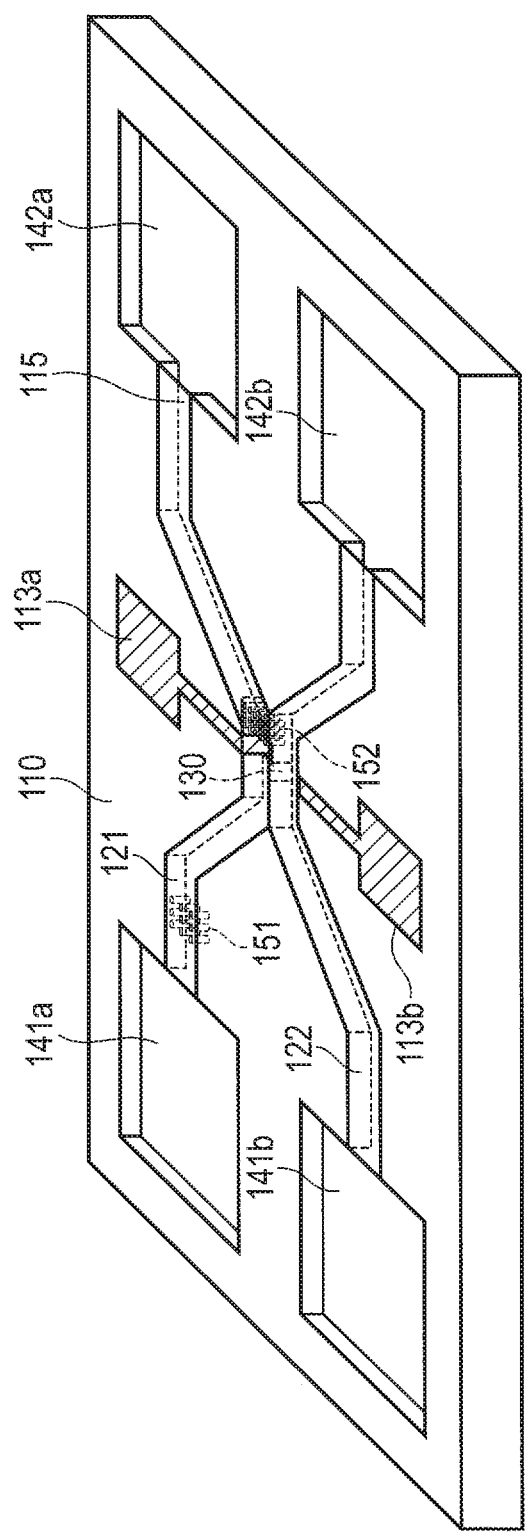
F I G. 19

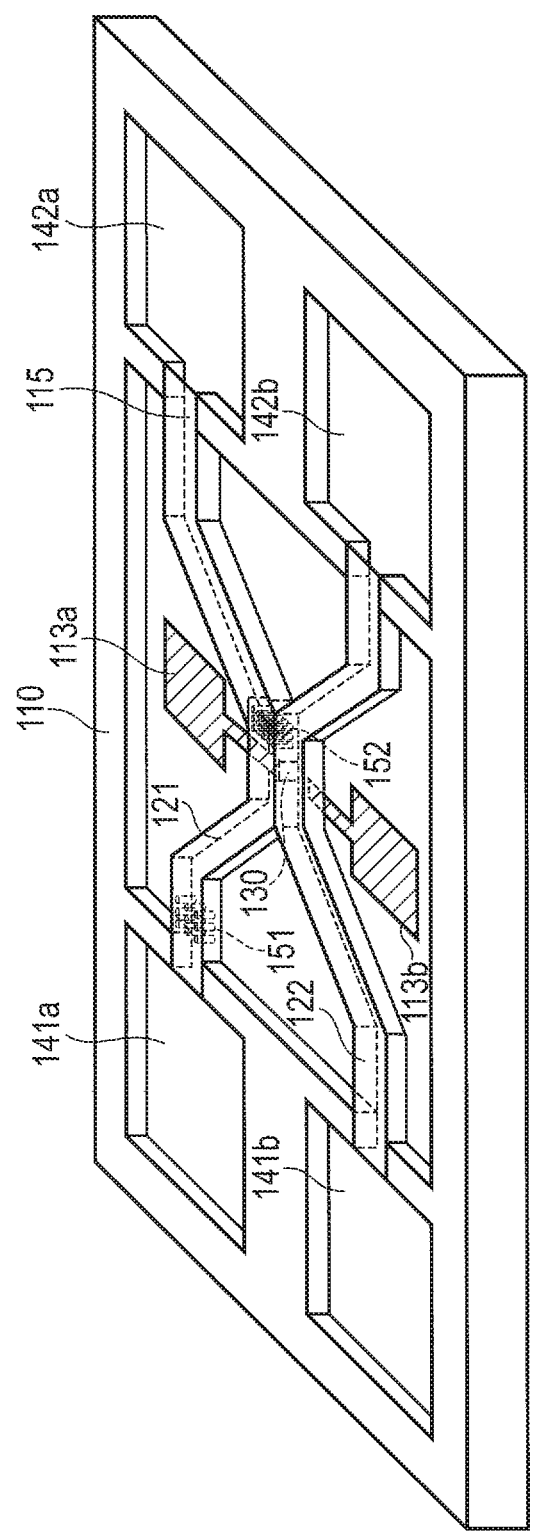
F I G. 22

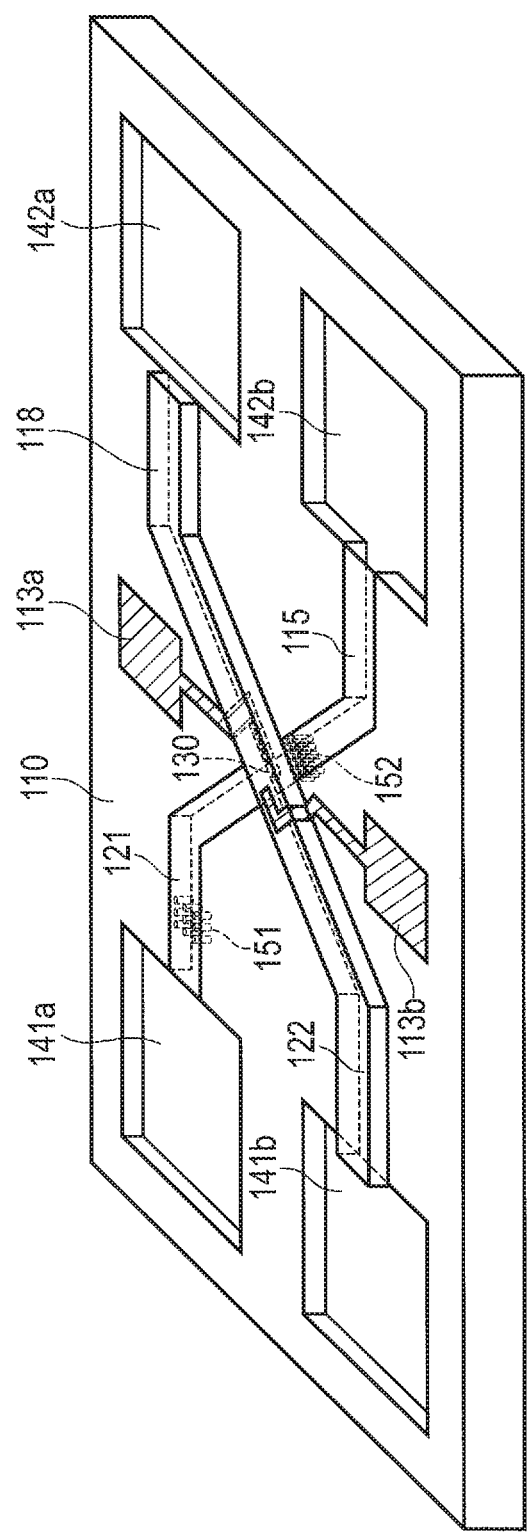
F I G. 24

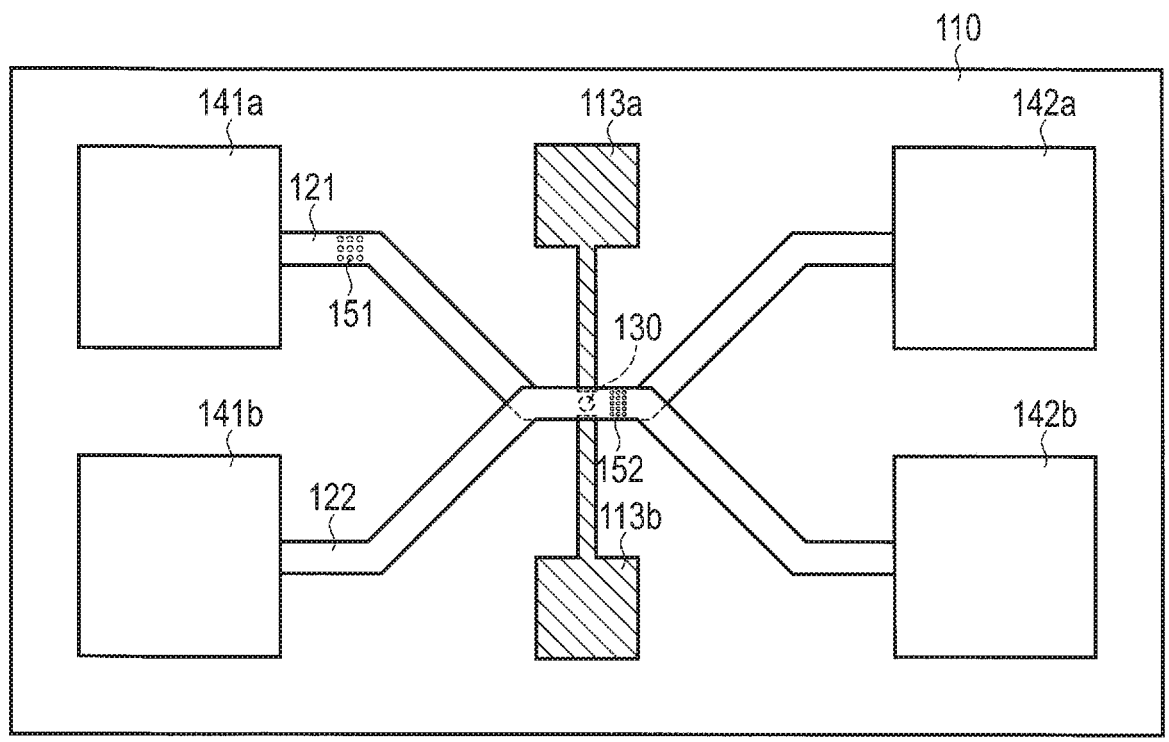
F I G. 26

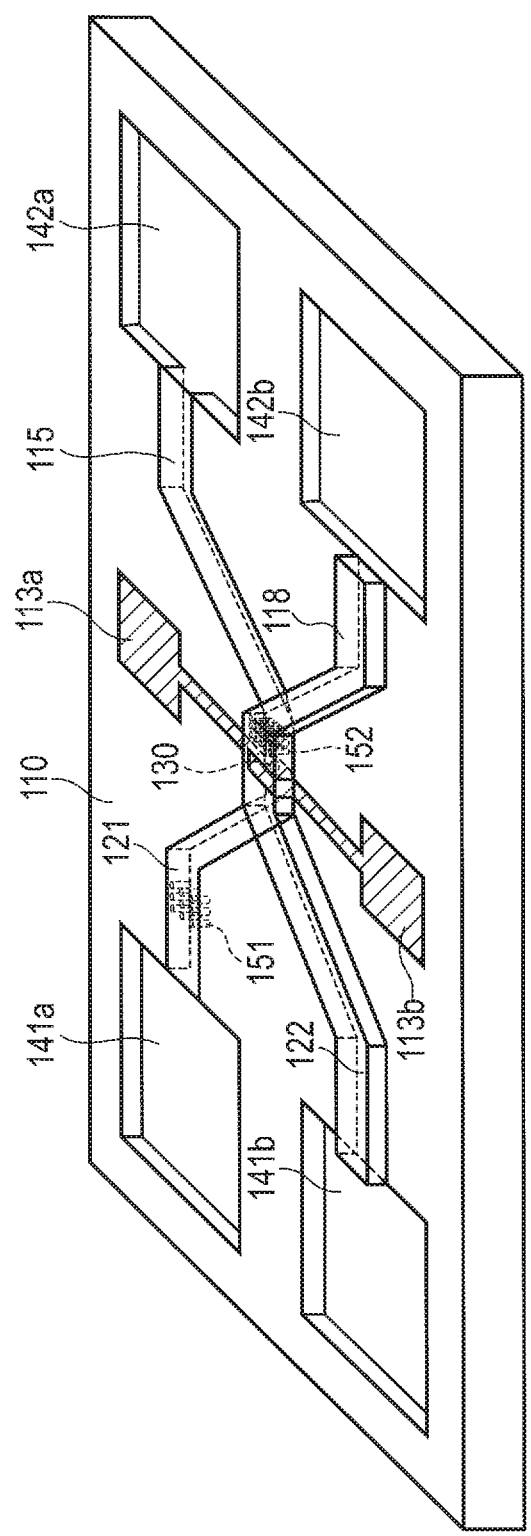
F I G. 27

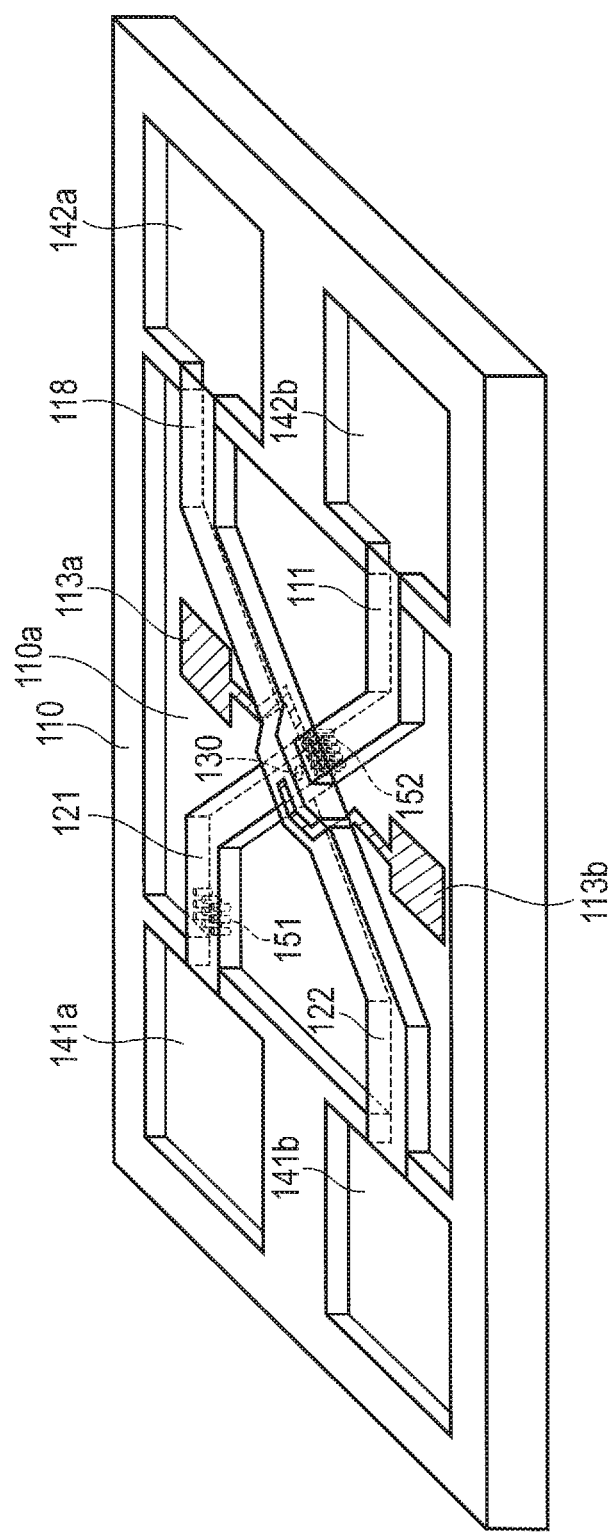
F I G. 30

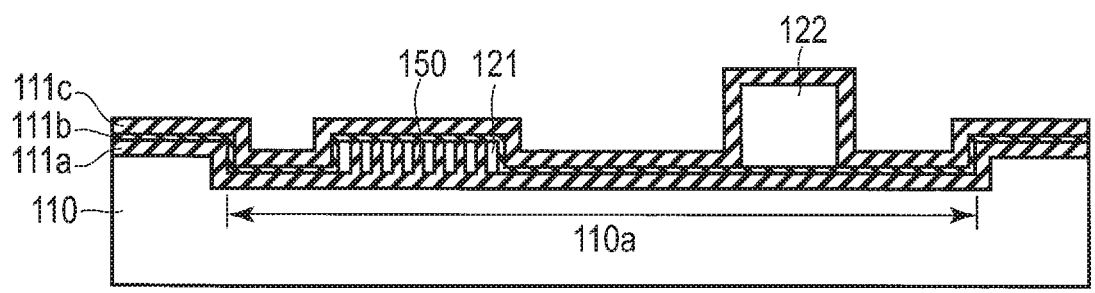
F I G. 32A
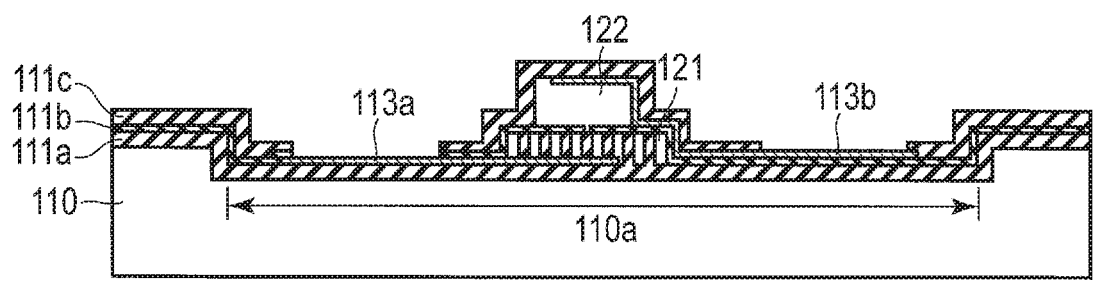
F I G. 32B

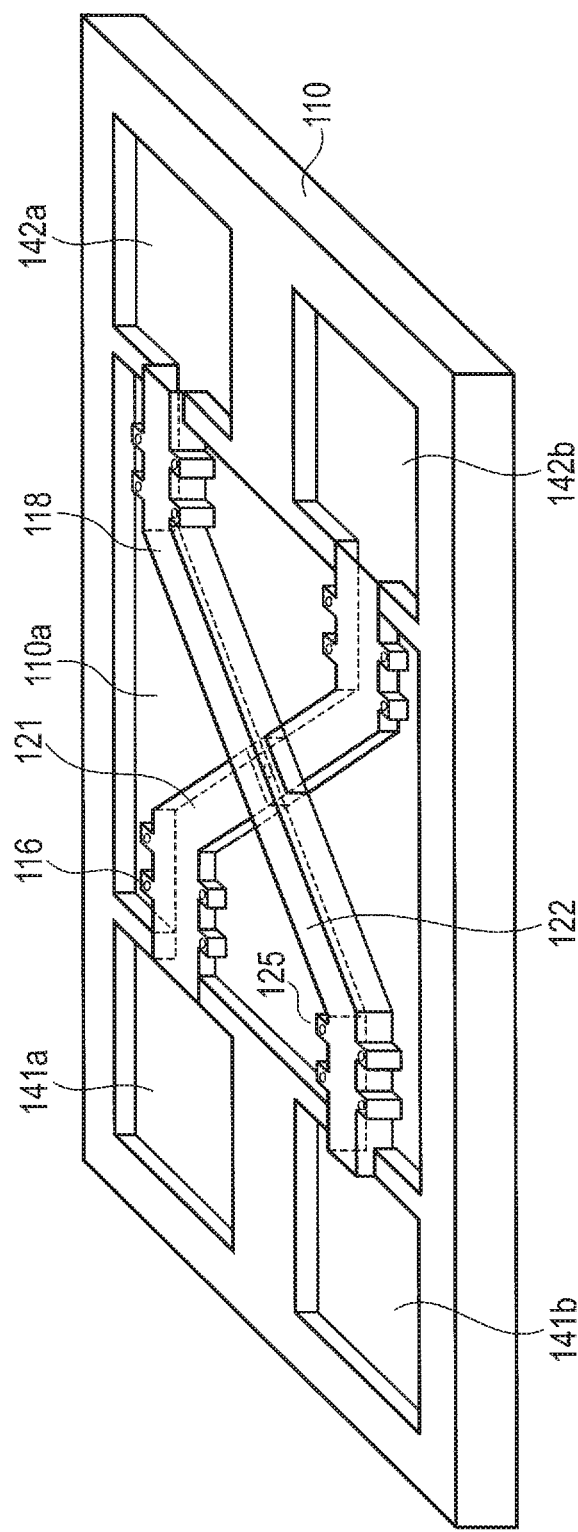
F I G. 33

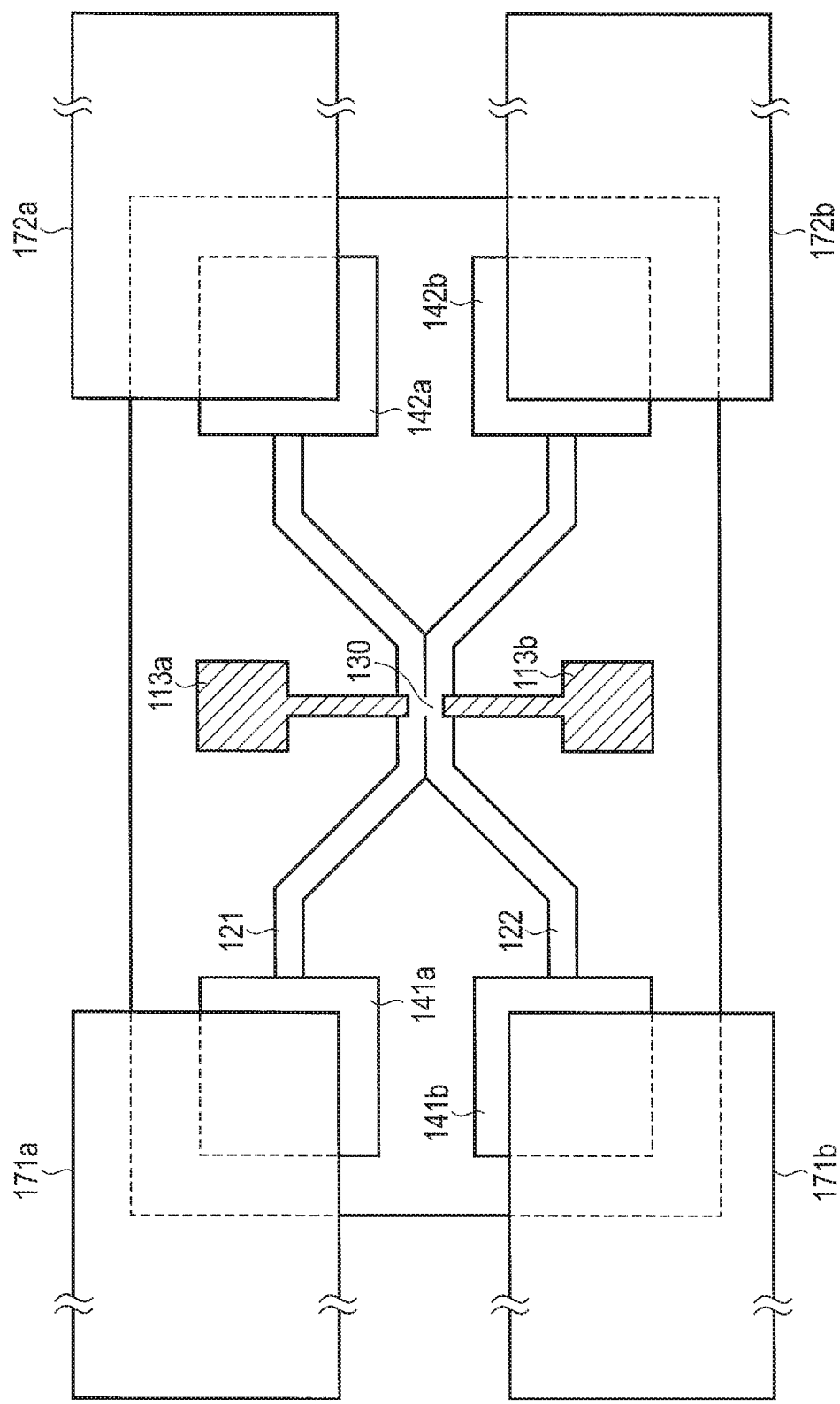
F I G. 34

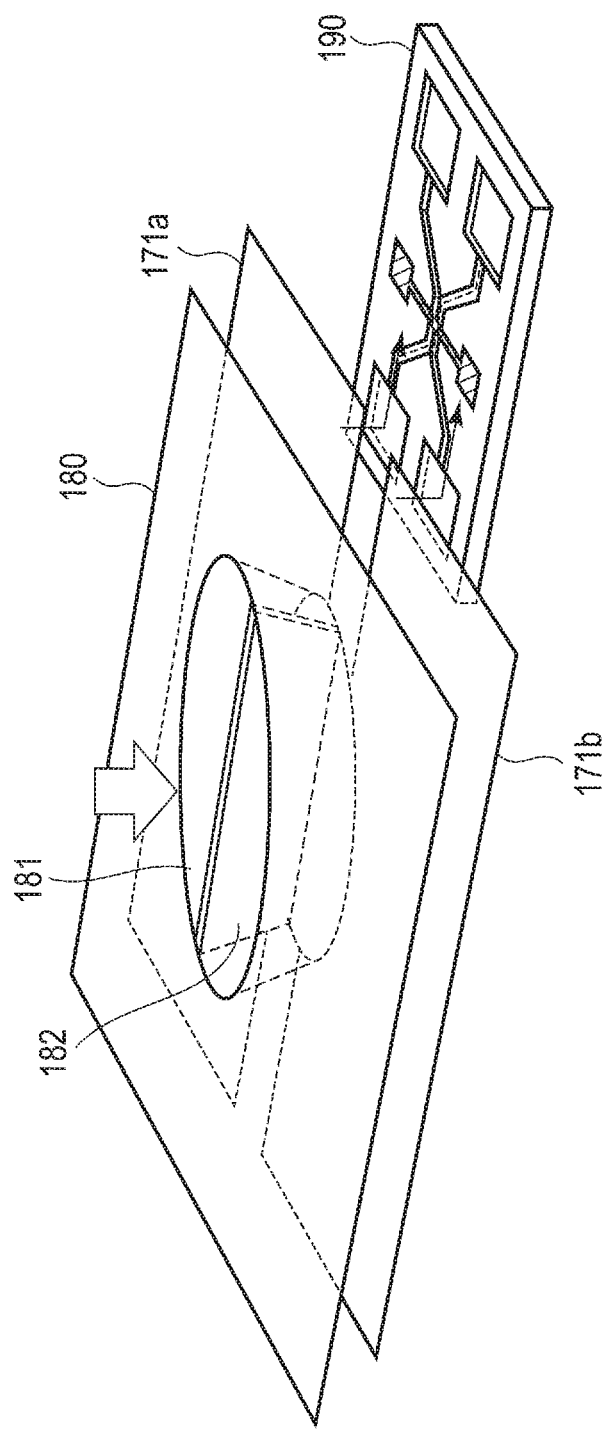
F I G. 36

US 10,533,934 B2

PARTICLE INSPECTION SYSTEM AND DRIVING METHOD EMPLOYED THEREIN

CROSS REFERENCE TO RELATED APPLICATIONS

This application is a Continuation Application of PCT Application No. PCT/JP2015/057606, filed Mar. 10, 2015 and based upon and claiming the benefit of priority from Japanese Patent Application No. 2014-147614, filed Jul. 18, 2014, the entire contents of all of which are incorporated herein by reference.

FIELD

Embodiments described herein relate generally to a particle inspection system and a driving method thereof.

BACKGROUND

Recently, in such technical fields as biotechnology and healthcare, attention is being paid to micro-analysis chips which, by means of fine fluid elements, such as micro flow channels and detection mechanisms, electrically detects fine particles or biopolymers in a sample liquid, or separates such components from the sample liquid. The separation/detection mechanisms of this type of analysis chips often include a mechanism for applying an electrical signal to a sample liquid which has been introduced between electrodes, and/or extracting a characteristic change in a sample liquid as an electrical signal.

However, since the sample liquid directly contacts the electrodes, there is a case where the sample liquid may electrochemically react with the electrodes as a result of the voltage applied across the electrodes, thereby changing the nature of the surfaces of the electrodes. If the electrode surfaces are changed in this way, a problem that a necessary electrical signal is not applied to the sample liquid or a desired electrical signal is not obtained may occur.

BRIEF DESCRIPTION OF THE DRAWINGS

FIG. 11 is a circuit diagram showing an example of a current driving circuit used in the particle inspection system of FIG. 8;

FIG. 12 is a schematic block diagram showing a particle inspection system according to a third embodiment;

FIG. 17 is a schematic perspective view showing the structure of the third semiconductor micro-analysis chip;

FIG. 19 is a schematic perspective view showing the structure of the fourth semiconductor micro-analysis chip;

FIG. 22 is a schematic perspective view showing the structure of a fifth semiconductor micro-analysis chip;

FIG. 24 is a schematic perspective view showing the structure of the sixth semiconductor micro-analysis chip;

FIG. 26 is a plan view showing a modification of the sixth semiconductor micro-analysis chip;

FIG. 27 is a perspective view showing the modification of the sixth semiconductor micro-analysis chip;

FIG. 30 is a schematic perspective view showing the structure of a seventh semiconductor micro-analysis chip;

FIGS. 32A and 32B are schematic cross-sectional views showing the structure of the eighth semiconductor micro-analysis chip;

FIG. 33 is a schematic perspective view showing the structure of a ninth semiconductor micro-analysis chip;

FIG. 34 is a schematic plan view showing the structure of a tenth semiconductor micro-analysis chip;

FIG. 36 is a schematic perspective view showing the structure of the eleventh semiconductor micro-analysis chip.

DETAILED DESCRIPTION

In general, according to one embodiment, a particle inspection system comprises: a voltage driving circuit which applies a driving voltage for a particle inspection to a particle inspection chip which detects a fine particle in a sample liquid and outputs a current signal indicative of the fine particle; a current-voltage conversion circuit which converts, into a voltage signal, the current signal output from the particle inspection chip when the driving voltage is applied to the particle inspection chip; a detection circuit which detects, based on the voltage signal, whether the sample liquid is introduced into a detection region of the particle inspection chip; and an analysis circuit which analyzes the fine particle in the sample liquid based on the voltage signal. The voltage driving circuit varies the driving voltage based on the detection result of the detection circuit.

Embodiments will be described in detail with reference to the accompanying drawings.

In the following drawings, like reference numbers denote like elements. However, it should be noted that the drawings are schematic ones, in which the dimensional relationship between thicknesses and planar sizes, and the ratio in thickness between layers, may differ from the actual ones. Therefore, specific thicknesses and/or sizes should be determined considering the description below.

Further, the relationships in dimension, the ratio in thickness between layers, etc., may vary between the figures. Yet further, descriptions have been given of specific materials and/or structures just as examples, and the materials and/or structures can be replaced with other one having the same functions. Thus, the embodiments are not limited to the described ones.

(First Embodiment)

Figure 1:
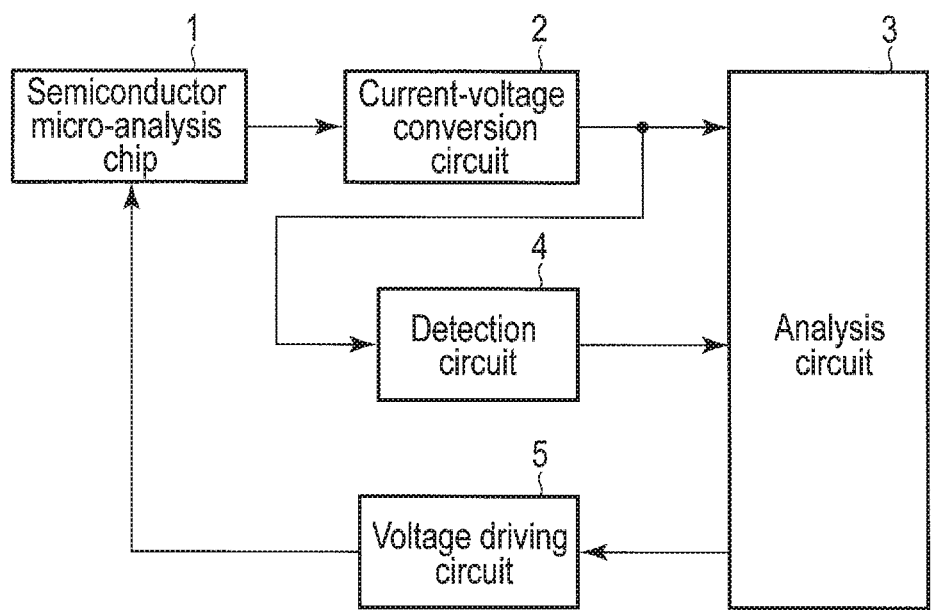
FIG. 1 is a schematic block diagram showing a particle inspection system according to a first embodiment.

FIG. 1 is a schematic block diagram showing a particle inspection system according to a first embodiment. The particle inspection system of the first embodiment comprises a semiconductor micro-analysis chip 1 and various circuits 2 to 5.

Figure 2:
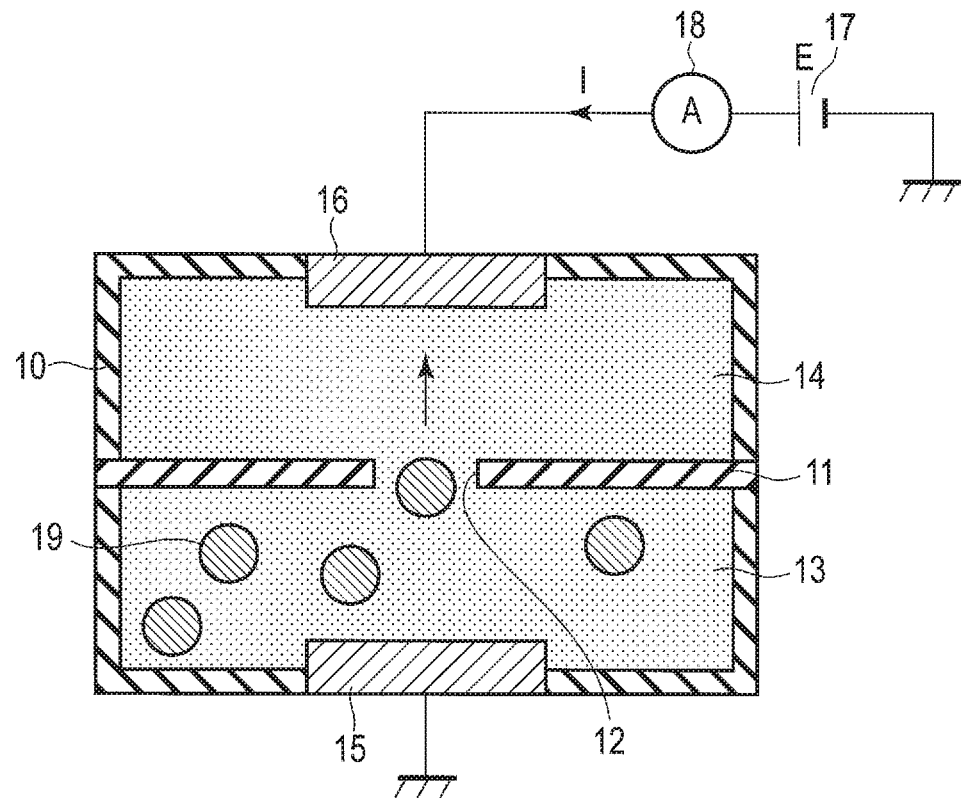
FIG. 2 is a schematic cross-sectional view showing the structure of a semiconductor micro-analysis chip used in the particle inspection system of FIG. 1.

The semiconductor micro-analysis chip 1 is constructed as schematically shown in FIG. 2. The interior of a case 10 is partitioned into a first region 13 and a second region 14 by an insulating partition 11. The partition 11 has a micropore 12 that permits the first and second regions 13 and 14 to communicate with each other. The size of the micropore 12 is set greater than a to-be-detected object (fine particle) 19, such as a fine particle or a biopolymer. The thickness of the partition 11 is set thinner than the to-be-detected object 19. The to-be-detected object will hereinafter be referred to as a target object.

A first electrode 15 and a second electrode 16 are provided on walls of the case 10. The first electrode 15 has a portion thereof exposed to the first region 13, while the second electrode 16 has a portion thereof exposed to the second region 14. A power supply 17 is used to apply a voltage between the first and second electrodes 15 and 16. The current flowing through the electrodes 15 and 16 is detected by an ampere meter 18.

It is sufficient if the entire case 10 is formed of an electrically and chemically inactive material. Alternatively, the inner surface of the case defining the first region 13, the inner surface of the case defining the second region 14, the contact portion of the case and the first electrode 15, and the contact portion of the case and the first electrode 16 may be formed of an electrically and chemically inactive material. For instance, SiN, $SiO_2$, $Al_2O_3$, glass, sapphire, ceramic, plastic, fluorine resin, rubber, elastomer, etc., can be used as the material of the case 10.

Further, it is sufficient if the partition 11 is formed of an electrically chemically inactive and insulating material. For instance, it is sufficient if the partition 11 is formed of SiN, $SiO_2$, $Al_2O_3$, glass, sapphire, ceramic, plastic, fluorine resin, rubber, elastomer, etc. It is more preferable to select a material that is inexpensive and can be treated in a mass-production-enabled semiconductor process.

Further, a conductive metal, such as Pt, Ir, Pd, Au, Hg, Sn, Cu, Zn, Fe, Mg, Co, Ni, V and calomel, and any appropriate combination thereof, is used as the material of the first and second electrodes 15 and 16. Further, electrochemical electrodes, such as Ag/AgCl or Hg/HgO, can also be used, it is more preferable to select, from these materials, a material that is inexpensive and can be treated in a mass-production-enabled semiconductor process. The first and second electrodes 15 and 16 may differ or be the same in size and/or shape.

A conductive sample liquid containing a target object 19 is introduced into the first and second regions 13 and 14. At this time, a liquid can flow between the first and second regions 13 and 14 through the micropore 12. Further, parts of the first and second electrodes 15 and 16 are soaked with the liquid introduced into the first and second regions 13 and 14, respectively. As the conductive sample liquid, an electrolyte solution, such as a KCl aqueous solution, or a buffer solution, such as a TE (Tris Ethylene diamine tetra acetic acid) buffer solution or PBS (Phosphate Buffered Saline) buffer solution, can be used. Introduction of the liquid into the first and second regions 13 and 14 can be realized utilizing a capillary phenomenon based on a fine flow channel, an external pump, or an electro-osmotic flow that occurs during applying an electric field to a liquid.

Figure 3:
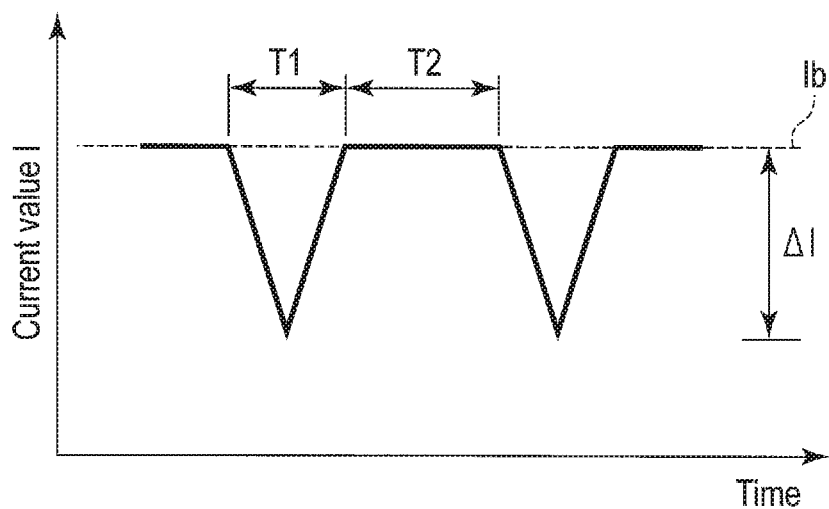
FIG. 3 is a signal waveform chart showing changes in current signal assumed when a fine particle has passed through a micropore formed in a semiconductor micro-analysis chip.

FIG. 3 is a schematic view showing changes with time in an ionic current flowing through the first and second electrodes 15 and 16, assumed when a voltage is applied across the first and second electrodes 15 and 16, with the conductive sample liquid containing the target object 19 introduced into the first and second regions 13 and 14. For convenience sake, a region between the first and second electrodes 15 and 16, into which the conductive sample liquid is introduced to thereby cause the flow of the ionic current, will be referred to as a detection region. The base current value of the ionic current is a value Ib determined from, for example, the conductivity of the conductive sample liquid, and the sizes of the first electrode 15, the second electrode 16, the first region 13, the second region 14 and the micropore 12. When the target object 19 passes through the micropore 12, the ionic current varies from the base current value Ib.

More specifically, assume, for example, that the potential of the second electrode 16 is higher than that of the first electrode, and the target object 19 is negatively charged. In this case, the target object 19 positioning in the first region 13 is moved through the micropore 12 to the second region 14 by the electric field generated between the first and second electrodes 15 and 16. When the target object 19 passes through the micropore 12, part of the micropore 12 is blocked by the target object 19, whereby the current path of the ionic current is limited. As a result, the ionic current becomes lower than the base current value Ib.

A change ΔI in the ionic current relative to the base current value Ib, and a time T1 required for the ionic current value to vary, vary depending upon the size of the target object 19. Further, the time interval T2 of a change in the ionic current corresponds to the distance between target objects 19 passing through the micropore 12. By measuring ΔI, T1 and T2 from the ionic current of the semiconductor micro-analysis chip 1, the target object 19 can be analyzed.

The velocity V of the target object 19 passing through the micropore 12 can be approximated by the following equation (1), and the velocity V is a factor for determining the time T1 required for the ionic current to vary:

$$V = A \cdot B \cdot \xi \cdot I \qquad (1)$$

where A is a constant determined from the type of the conductive sample liquid, B is a constant determined from the size of the micropore 12, ξ is the zeta potential of the target 19 in the conductive sample liquid, and I is the ionic current flowing through the micropore 12. From equation (1), the velocity V of the target object 19 passing through the micropore 12 is proportional to the ionic current I flowing through the micropore 12. Namely, when the ionic current I has varied, the velocity V varies even if the size of the target object 19 does not change, whereby the time T1 required for the ionic current to vary. This means that if the ionic current I has varied from the base current Ib, the target object 19 cannot be accurately analyzed.

A main factor that causes a change in the ionic current I is, for example, an increase in interface resistance due to a change in the nature of the surfaces of the first and second electrodes 15 and 16. The change in the nature of the surfaces will be caused by an electrochemical reaction between the conductive sample liquid and the first and second electrodes 15 and 16. As the current flowing through the conductive sample liquid increases, the reaction occurs more easily.

Figure 4:
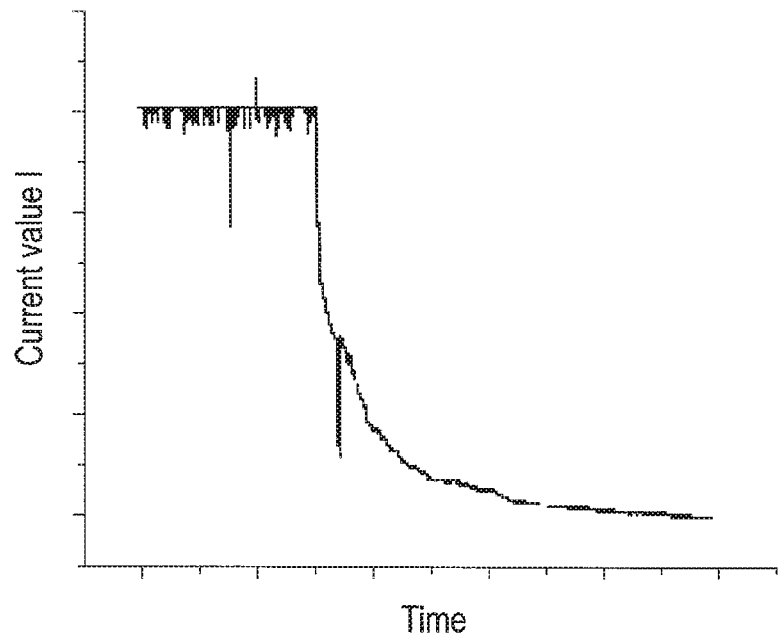
FIG. 4 is a signal waveform chart showing changes in current signal assumed when a sample liquid has introduced into the semiconductor micro-analysis chip.

As shown in FIG. 4, a conductive sample liquid is introduced into the detection region, with an excessive voltage applied across the first and second electrodes 15 and 16. At this time, the chip resistance between the first and second electrodes 15 and 16 rapidly drops, and the electrostatic capacitance rapidly rises. Accordingly, an excessive current flows through the first and second electrodes 15 and 16, whereby the above-mentioned electrochemical reaction occurs at the first and second electrodes 15 and 16. As a result, the ionic current I (ion base current Ib) is reduced.

To suppress changes in the nature of the surfaces of the first and second electrodes 15 and 16, it is necessary to set, to a low value, the ionic current I flowing through the first and second electrodes 15 and 16, immediately after the conductive sample liquid is introduced into the detection region. In other words, a driving voltage applied across the first and second electrodes 15 and 16 must be set lower before the introduction of the conductive sample liquid into the detection region, than after the introduction.

In the first embodiment, the driving voltage applied across the first and second electrodes 15 and 16 of the semiconductor micro-analysis chip 1 is varied before and after the above introduction of the conductive sample liquid into the detection region.

As shown in FIG. 1, the first embodiment comprises a current-voltage conversion circuit 2 that converts the ionic current I of the semiconductor micro-analysis chip 1, an analysis circuit 3 that analyzes the target object 19 based on the voltage signal output from the current-voltage conversion circuit 2, a detection circuit 4 that detects whether the conductive sample liquid has been introduced into the detection region, based on the voltage signal output from the current-voltage conversion circuit 2, and a voltage driving circuit 5 that applies a voltage across the first and second electrodes 15 and 16 of the semiconductor micro-analysis chip 1. The analysis circuit 3 analyzes the target object 19 based on the voltage signal, also determines whether the conductive sample liquid has been introduced into the detection region, based on the detection result of the detection circuit 4, and informs the voltage driving circuit 5 that the conductive sample liquid has been introduced into the detection region.

Figure 5:
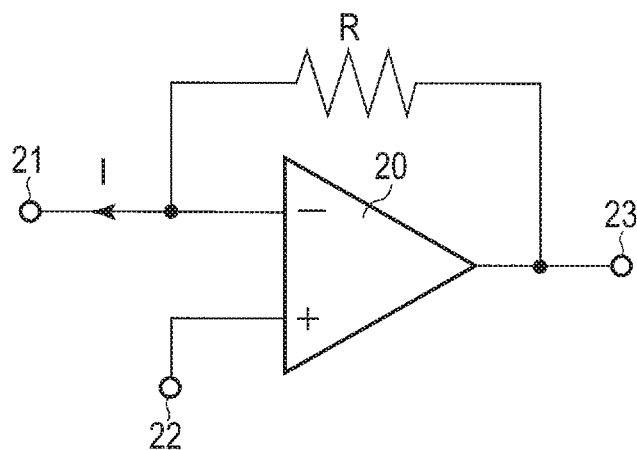
FIG. 5 is a circuit diagram showing an example of a current-voltage conversion circuit used in the particle inspection system of FIG. 1.

As shown in, for example, FIG. 5, the current-voltage conversion circuit 2 is a so-called transimpedance amplifier comprising a differential amplifier 20 and a resistor R. One of the first and second electrodes 15 and 16 of the semiconductor micro-analysis chip 1 is connected to a terminal 21, and the other of them is grounded. The driving voltage applied across the first and second electrodes 15 and 16 is input to a terminal 22. By this structure, the driving voltage input to the terminal 22 is applied to the terminal 21, whereby the driving voltage is applied to the semiconductor micro-analysis chip 1. The voltage value V of the voltage signal output from a terminal 23 at this time is given by $$V = RI + E \qquad (2)$$

where I is the ionic current flowing through the first and second electrodes 15 and 16.

From the above equation (2), the voltage value V of the voltage signal at the terminal 23 is E before the introduction of the conductive sample liquid into the detection region. After the introduction of the conductive sample liquid, the voltage value V becomes the sum of E and the product of the ionic current I and the resistance R. Namely, the voltage value of the voltage signal at the terminal 23 varies before and after the introduction of the conductive sample liquid into the detection region.

There is a case where in the current-voltage conversion circuit 2 shown in FIG. 5, a capacitor is connected in parallel with the resistor R or another additional element is added in order to secure circuit stability, such as suppression of circuit anomalous oscillation utilizing a feedback loop. Further, the current-voltage conversion circuit 2 is not limited to the transimpedance amplifier. It is sufficient if the circuit 2 is a circuit in which the voltage value of the voltage signal output from the terminal 23 varies before and after the introduction of the conductive sample liquid into the detection region.

Figure 6:
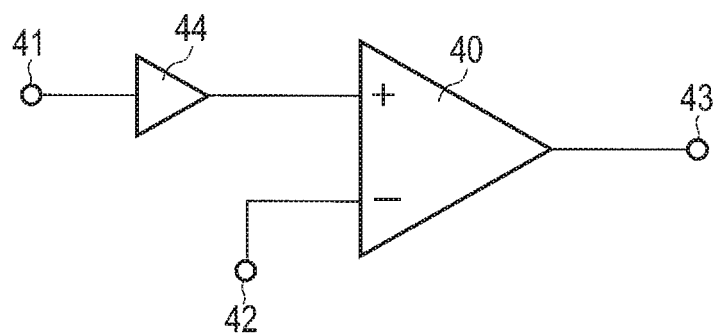
FIG. 6 is a circuit diagram showing an example of an inspection circuit used in the particle inspection system of FIG. 1.

As shown in, for example, FIG. 6, the detection circuit 4 comprises a comparator 40 and an amplifier 44. The terminal 23 of the current-voltage conversion circuit 2 is connected to the input terminal 41 of the amplifier 44. A signal having its voltage amplified by the amplifier 44 is input to the +terminal (noninverting terminal) of the comparator 40. A reference voltage is input to the −terminal 42 of the comparator 40. The reference voltage is set to a level between the levels of the voltages applied to the +terminal of the comparator 40 before and after the introduction of the conductive sample liquid into the detection region. By this setting, the output terminal 43 of the detection circuit 4 assumes a low level before the introduction of the conductive sample liquid into the detection region, and assumes a high level after the introduction. Accordingly, it can be detected from the output level of the output terminal 43 whether the sample liquid has been introduced.

The detection circuit 4 shown in FIG. 6 may further comprise an additional element for imparting hysteresis characteristics to the comparator 40 in order to enhance the noise tolerances of the voltage signal input to the terminal 41, and/or for securing circuit stability. Further, the detection circuit 4 may not incorporate the amplifier 44, depending upon the level of the voltage applied to the terminal 41. Yet further, it is sufficient if the detection circuit 4 is constructed such that the output level of the terminal 43 varies when the conductive sample liquid has been introduced into the detection region.

Figure 7:
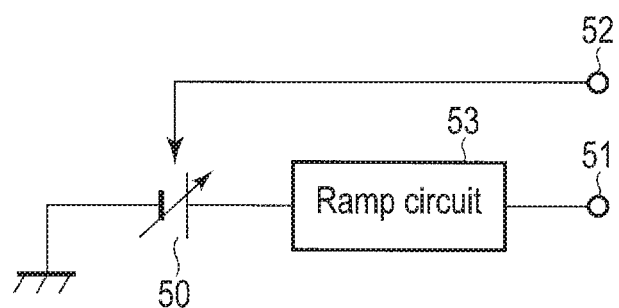
FIG. 7 is a circuit diagram showing an example of a voltage driving circuit used in the particle inspection system of FIG. 1.

As shown in, for example, FIG. 7, the voltage driving circuit 5 comprises a variable power supply 50 and a ramp circuit 53. The variable power supply 50 has a function of varying a voltage in accordance with a signal input to a terminal 52. The ramp circuit 53 has a function of varying the voltage change in the variable power supply 50 smoothly like a ramp. The output terminal 51 of the ramp circuit 53 is connected to the terminal 22 of the current-voltage conversion circuit 2. Namely, the voltage driving circuit 5 applies a driving voltage to the semiconductor micro-analysis chip 1. As a result, the driving voltage applied to the semiconductor micro-analysis chip 1 can be varied by changing a signal, input to the terminal 52, before and after the introduction of the conductive sample liquid into the detection region of the semiconductor micro-analysis chip 1.

More specifically, the voltage at the terminal 51 when the output terminal 43 of the detection circuit 4 is at a low level is made lower than the voltage at the terminal 51 when the output terminal 43 is at a high level. The voltage at the terminal 51 is appropriately set in accordance with the type of the sample liquid introduced into the detection region, and the type of the first and second electrodes 15 and 16. By this setting, changes in the nature of the surfaces of the first and second electrodes 15 and 16 immediately after the introduction of the conductive sample liquid into the detection region can be suppressed.

The ramp circuit 53 of FIG. 7 can change the output change of the variable power supply 50 smoothly like a ramp, using a charge/discharge circuit provided with, for example, a capacitor, and also can change the same stepwise or exponentially. Further, the time required for a change made in a ramp manner, i.e., the time required for the driving voltage before the introduction of the conductive sample liquid into the detection region to shift to the driving voltage after the introduction, is set greater than a time constant determined from the electrostatic capacitance and the chip resistance of the semiconductor micro-analysis chip 1. Namely, the above-mentioned time is set not less than 10 μs that is greater than the time constant, since the electrostatic capacitance of the semiconductor micro-analysis chip 1 is about 1 pF and the chip resistance is about 10 MΩ. By this structure, changes in ionic current can be more reduced, thereby suppressing changes in the nature of the surfaces of the first and second electrodes 15 and 16 soaked in the conductive sample liquid.

Since the change in the ionic current input to the current-voltage conversion circuit 2 varies smoothly like a ramp when the driving voltage varies smoothly like a ramp, the current-voltage conversion circuit 2 can be protected from, for example, a breakage due to rapid change in the ionic current. If the variable power supply 50 has a function of varying the voltage change like the ramp circuit 53, no ramp circuit 53 is necessary.

The analysis circuit 3 comprises a micro computer, a personal computer, a work station, a logic circuit or a sequencer, which incorporates an A/D converter, a comparator, a counter, a processor, etc., so as to perform measurement and analysis associated with the change ΔI in the ionic current, the time T1 required for the ionic current to vary, and the time interval 12 in which the ionic current varies, which are shown in FIG. 3. The analysis circuit 3 further comprises a memory for storing measurement results and comparative information, a display unit for displaying analysis results, and an input/output terminal for transmitting and receiving information, such as analysis results, to and from an external unit.

The analysis circuit 3 receives a voltage signal from the current-voltage conversion circuit 2. The analysis circuit 3 performs the above-mentioned analysis based on the voltage signal. The analysis circuit 3 is connected to the output terminal 43 of the detection circuit 4 and the terminal 52 of the voltage driving circuit 5. A detection signal indicative of the introduction of the conductive sample liquid, into the detection region is transmitted from the detection circuit 4 to the voltage driving circuit 5 via the analysis circuit 3. Even if the detection circuit 4 is directly connected to the voltage driving circuit 5, no problem will occur in suppressing changes in the nature of the surfaces of the first and second electrodes 15 and 16 soaked in the conductive sample liquid. However, since a detection signal is sent from the detection circuit 4 to the analysis circuit 3, the analysis circuit 3 can analyze the sample liquid based on the detection signal. Thus, the sample liquid can be analyzed more accurately.

Figure 8:
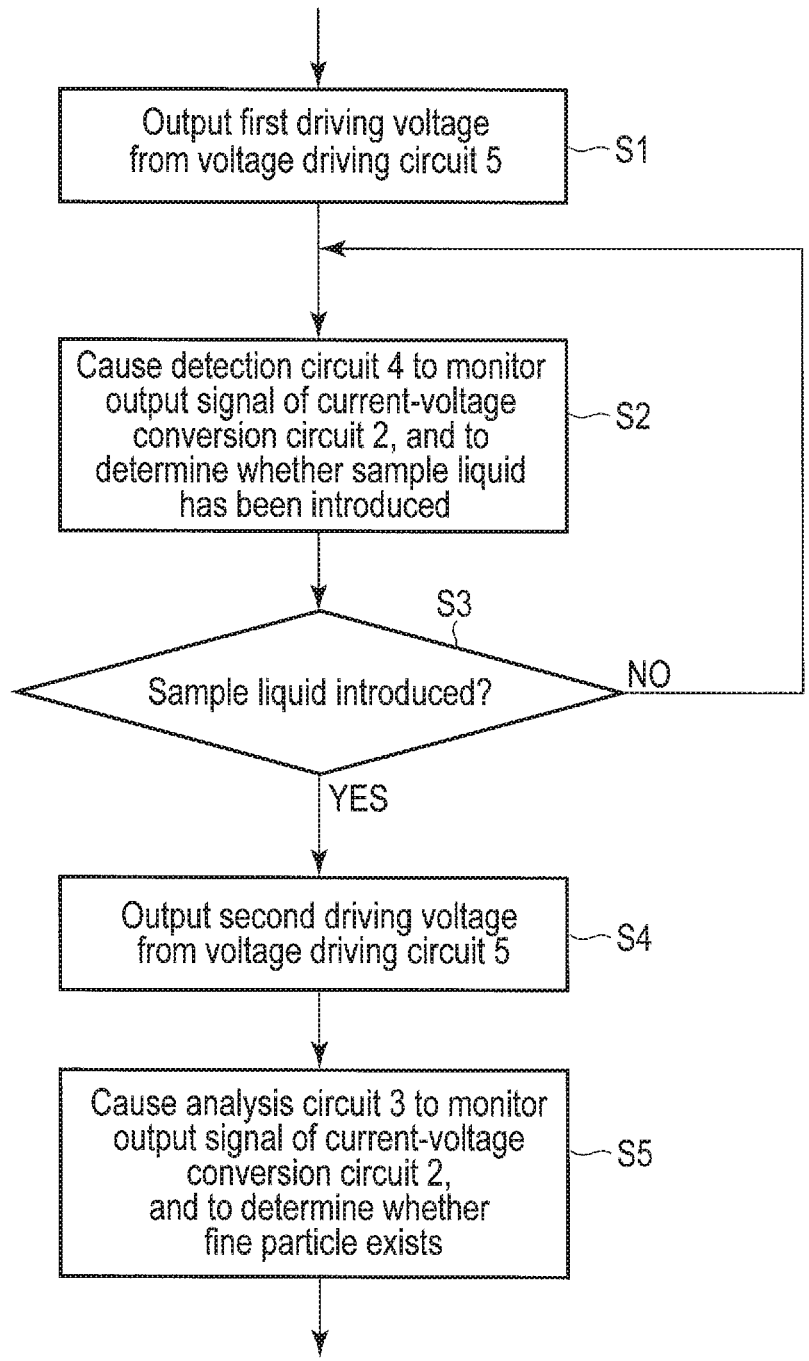
FIG. 8 is a flowchart for explaining a particle inspection method using the particle inspection system of FIG. 1.

Referring then to the flowchart of FIG. 8, a description will be given of a fine particle inspection method using the particle inspection system constructed as the above.

Firstly, in accordance with an instruction from the analysis circuit 3, the voltage driving circuit 5 outputs a first driving voltage and applies it to the semiconductor micro-analysis chip 1 (step S1). More specifically, the first electrode 15 of the semiconductor micro-analysis chip 1 is grounded, and the first driving voltage is applied to the second electrode of the same. The first driving voltage is sufficiently lower than a voltage for detecting fine particles. Namely, the first driving voltage is set to a value at which the nature of the surfaces of the first and second electrodes 15 and 16 is not changed by the current flowing through the electrodes 15 and 16 when the sample liquid has been introduced into the detection region.

On the other hand, the current-voltage conversion circuit 2 converts the output current of the semiconductor micro-analysis chip 1 into a voltage, and sends a signal indicative of the voltage to the analysis circuit 3 and the detection circuit 4.

Subsequently, a sample liquid is introduced into the detection region of the semiconductor micro-analysis chip 1. At this time, the detection circuit 4 monitors the voltage signal output from the current-voltage conversion circuit 2 (step S2), and determines whether a sample liquid has been introduced into the detection region (step S3).

If the detection circuit 4 has determined that the sample liquid has been introduced into the detection region, it provides the analysis circuit 3 with a signal indicating that the sample liquid has been introduced. Upon receiving this signal, the analysis circuit 3 instructs the voltage driving circuit to output a second driving voltage.

In response to the instruction from the analysis circuit 3, the voltage driving circuit 5 outputs the second driving voltage and applies the same to the semiconductor micro-analysis chip 1 (step S4). The second driving voltage is appropriate for the detection of fine particles, and is higher than the first driving voltage.

After that, the analysis circuit 3 analyzes the voltage signal output from the current-voltage conversion circuit 2, with the second driving voltage applied to the semiconductor micro-analysis chip 1. Based on a level change in voltage signal, it is determined whether fine particles exist. (Step S5). Thus, fine particles in the sample liquid introduced into the semiconductor micro-analysis chip 1 can be inspected.

As described above, in the first embodiment, the driving voltage applied across the first and second electrodes 15 and 16 is varied before and after the introduction of the conductive sample liquid into the detection region of the semiconductor micro-analysis chip 1. More specifically, the first driving voltage applied before the introduction of the conductive sample liquid is set lower than the second driving voltage applied after the introduction of the conductive sample liquid. As a result, an excessive ionic current that will occur at the time of introduction of the sample liquid can be reduced. This can suppress variation in the ionic current caused by changes in the nature of the surfaces of the first and second electrodes 15 and 16 that will occur during the introduction of the sample liquid, thereby suppressing degradation of analysis accuracy with which the target object 19 is detected by the particle inspection system 1. In other words, the change in the electrode surfaces of the semiconductor micro-analysis chip, which will occur at the time of introduction of the sample liquid, can be suppressed to thereby enhance the reliability of the fine particle inspection. This has an extremely significant industrial worth.

In addition, the circuit elements used in the particle inspection system of the first embodiment can be produced by a widely utilized semiconductor device manufacturing process. Therefore, part of the elements or the entire elements can be formed integral with the semiconductor micro-analysis chip 1, which enables a compact particle inspection system to be realized.

(Second Embodiment)

Figure 9:
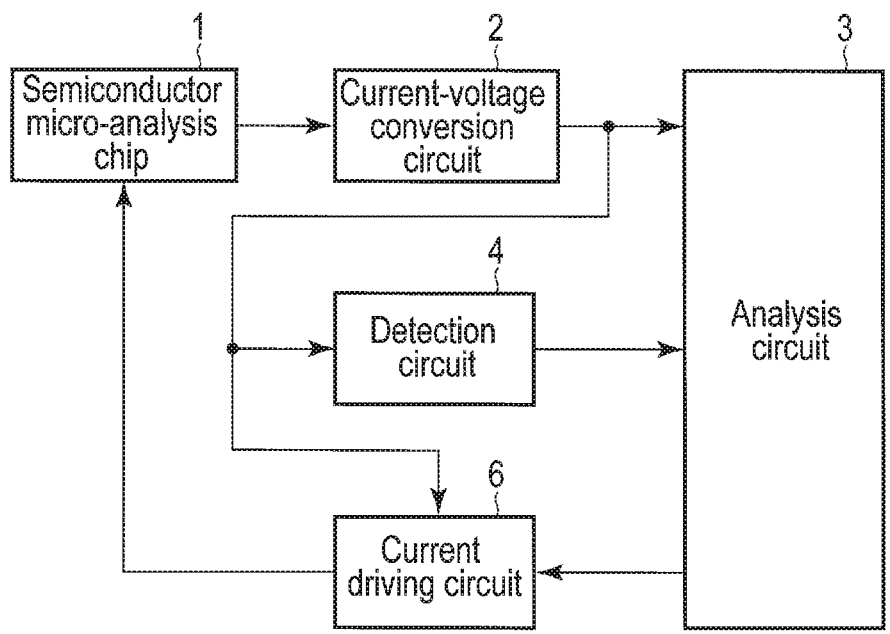
FIG. 9 is a schematic block diagram showing a particle inspection system according to a second embodiment.

FIG. 9 is a schematic block diagram showing a particle inspection system according to a second embodiment. In this figure, elements similar to those of FIG. 1 are denoted by corresponding reference numbers, and no detailed description will be given thereof.

The second embodiment differs from the first embodiment in that the former employs a current driving circuit 6 in place of the voltage driving circuit 5. The current driving circuit 6 has a function of receiving a voltage signal as the output of the current-voltage conversion circuit 2, and performing control to cause a constant current to flow into the detection region of the semiconductor micro-analysis chip 1. Further, the current driving circuit 6 can vary a driving voltage in accordance with an instruction from the analysis circuit 3, as in the above-described first embodiment. The driving voltage output from the current driving circuit 6 is applied to the semiconductor micro-analysis chip 1.

Figure 10:
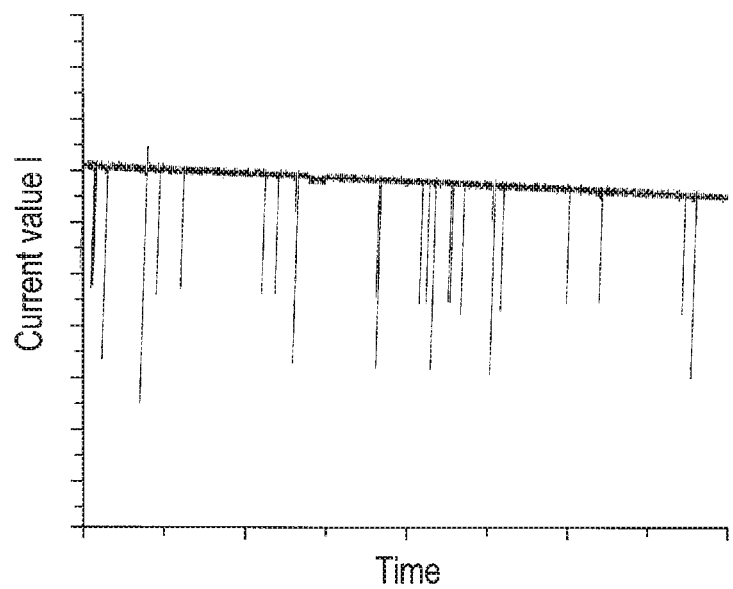
FIG. 10 is a signal waveform chart showing changes in the base current signal of the semiconductor micro-analysis chip.

FIG. 10 shows temporal variation in the ionic current I assumed when the conductive sample liquid has been introduced into the detection region of the semiconductor micro-analysis chip 1 to analyze the target object 19 in the analysis circuit 3. In FIG. 10, large changes result from the detection of fine particles, and small changes result from changes in base current.

It can be understood from FIG. 10 that even after a sufficient time from the introduction of the conductive sample liquid into the detection region, the nature of the surfaces of the first and second electrodes 15 and 16 slightly advances and the base ionic current gradually varies with time. Since the change in the base ionic current changes the velocity of the target object 19 passing through the micropore 12, as is expressed by the above equation (1), the analysis accuracy of the analysis circuit 3 associated with the target object 19 is degraded.

The current driving circuit 6 controls the driving voltage applied across the first and second electrodes 15 and 16 so as to suppress the change in the above-mentioned base ionic current Ib and make, constant, the base ionic current Ib of the semiconductor micro-analysis chip 1.

FIG. 11 shows a specific structure example of the current driving circuit 6. As shown, the circuit comprises, for example, an amplifier 61 connected to a terminal 60, a low-pass filter 62, a proportional-plus-integral circuit 600 and a reference power supply 67 having its voltage value varied by an input signal from a terminal 69. The proportional-plus-integral circuit 600 comprises adders 63 and 66, a proportional circuit 64 and an integration circuit 65, and is connected to a terminal 68.

The terminal 60 is connected to the output terminal 23 of the current-voltage conversion circuit 2. As a result, a voltage signal, into which the ionic current I is converted, is input to the current driving circuit 6. This voltage signal is once amplified to a desired level by the amplifier 61, and is then passed through the low-pass filter 62, whereby a component of the signal corresponding to the change in the ionic current having occurred when the target object 19 has passed through the micropore 12 is eliminated. Namely, the low-pass filter 62 passes substantially only the voltage signal component corresponding to the base ionic current Ib.

In the proportional-plus-integral circuit 600, the difference between the voltage of the reference power supply 67 and the voltage signal received from the low-pass filter 62 is calculated by the adder 63, and feedback amounts are determined using the proportional circuit 64 and the integration circuit 65. Further, the voltage of the reference power supply 67 and the feedback amounts are summed up by the adder 66. The terminal 68 is connected to the terminal 22 of the current-voltage conversion circuit 2. Furthermore, the terminal 69 receives a detection signal from the detection circuit 4 via the analysis circuit. 3, as in the first embodiment. This structure enables the voltage of the reference power supply 67 to vary when the conductive sample liquid has been introduced into the detection region of the semiconductor micro-analysis chip 1. The above circuit structure enables feedback control for causing a voltage signal output from the current-voltage conversion circuit 2 to approach the voltage of the reference power supply 67. As a result, the ionic current I can be maintained substantially constant to thereby suppress degradation of the analysis accuracy of the analysis circuit 3 associated with the target object 19, which results from changes in the ionic current I.

As described above, the ionic current I accords with the voltage of the reference power supply 67. Accordingly, the voltage of the reference power supply 67 is controlled by a signal input to the terminal 69 so that the voltage before the introduction of the conductive sample liquid into the detection region of the semiconductor micro-analysis chip 1 is lower than the voltage after the introduction of the same. By this control, the ionic current I flowing when the conductive sample liquid has been introduced into the detection region can be set small, and be thereafter increased to a desired value I. As a result, changes in the nature of the surfaces of the first, and second electrodes 15 and 16 can be suppressed.

It is more desirable to set the response time of the proportional-plus-integral circuit 600 so that the time required for the driving voltage before the introduction of the conductive sample liquid into the detection region to shift to the driving voltage after the introduction of the same is not less than 10 μs that is greater than a time constant determined from the electrostatic capacitance and chip resistance of the semiconductor micro-analysis chip 1.

The proportional-plus-integral circuit 600 is not limited to the circuit structure shown in FIG. 11. It is sufficient if the circuit. 600 can obtain a desired feedback amount. Further, the current driving circuit. 6 is not limited to the circuit structure shown in FIG. 11. It is sufficient if the circuit 6 can apply an appropriate driving voltage to the semiconductor micro-analysis chip 1.

As described above, in the second embodiment, an excessive ionic current, which occurs during the introduction of the sample liquid, can be reduced by reducing the driving voltage applied across the first and second electrodes 15 and 16 before the introduction of the conductive sample liquid into the detection region of the semiconductor micro-analysis chip 1, compared to the driving voltage applied across the first and second electrodes 15 and 16 after the introduction of the sample liquid. As a result, the same advantage as in the first embodiment can be obtained. Moreover, by applying a driving voltage to the semiconductor micro-analysis chip using the current driving circuit 6, degradation of the analysis accuracy of the analysis circuit 3 associated with the target object 19 due to a change in the ionic current I can be suppressed, whereby the analysis accuracy can be further enhanced.

In addition, the circuit elements used in the particle inspection system of the second embodiment can be produced by a widely utilized semiconductor device manufacturing process. Therefore, part of the elements or the entire elements can be formed integral with the semiconductor micro-analysis chip 1, which enables a compact particle inspection system to be realized.

(Third Embodiment)

As a further improvement of the second embodiment, the particle inspection system can be constructed as shown in FIG. 12.

The particle inspection system shown in FIG. 12 is obtained by changing the signal input to the detection circuit 4 from the output of the current-voltage conversion circuit 2 to the output of the current driving circuit 6. Namely, in the third embodiment, the detection circuit 4 is designed to detect whether a sample liquid has been introduced into the detection region of the semiconductor micro-analysis chip 1, based on the driving voltage applied to the current driving circuit 6.

By virtue of this circuit structure, when a certain response time of the current driving circuit 6 has elapsed after the conductive sample liquid is introduced into the detection region of the semiconductor micro-analysis chip 1, the detection circuit 4 detects the introduction of the sample liquid. As a result, the driving voltage is applied to the semiconductor micro-analysis chip 1 when a predetermined period time has elapsed after the introduction of the sample liquid.

This structure provides the advantage that changes in the nature of the surfaces of the first and second electrodes 15 and 16 can be more effectively suppressed, in addition to an advantage similar so that of the second embodiment.

(Examples of Particle Inspection Chip)

Examples of the semiconductor micro-analysis chip used for the inspection chip 1 of each of the above embodiments will now be described.

[First Semiconductor Micro-Analysis Chip]

Figure 13:
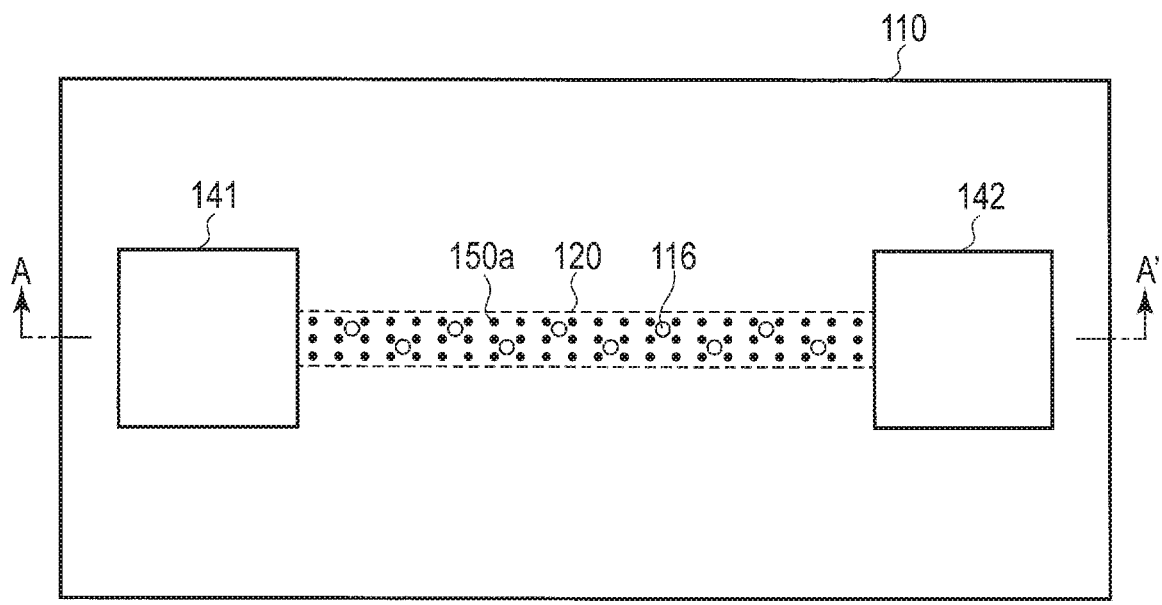
FIG. 13 is a schematic plan view showing the structure of a first semiconductor micro-analysis chip.
Figure 14:
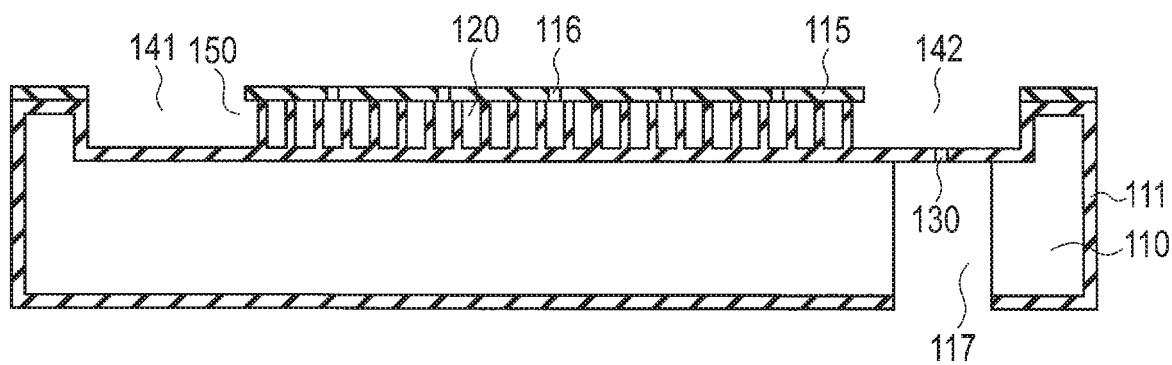
FIG. 14 is a cross-sectional view taken along line A-A' of FIG. 13.

FIGS. 13 and 14 are figures for describing a brief structure of a first semiconductor micro-analysis chip. FIG. 13 is a plan view, and FIG. 14 is a cross-sectional view taken along line A-A' of FIG. 13.

In the figures, reference number 110 denotes a semiconductor substrate. Various semiconductor materials, such as Si, Ge, SiC, GaAs, InP, and GaN, may be used for the substrate 110. In the following, an example in which Si is used for the semiconductor substrate 110 will be described.

On a surface portion of the Si substrate 110, a flow channel 120 formed of a linear groove is formed. The flow channel 120 is a channel in which a sample liquid including fine particles to be detected is made to flow, and is formed by etching a surface of the Si substrate 110 by, for example, 50 μm in width and 2 μm in depth. On both ends of the flow channel 120, an opening portion 141 and an opening portion 142 for introducing and discharging the sample liquid are provided, and electrodes can be inserted into the opening portions 141 and 142, respectively. At an area excluding the both ends of the flow channel 120, pillar array 150 is provided. The pillar array 150 is constituted by columnar structures (pillars) 150a extending from the bottom of the flow channel 120 to the surface of the Si substrate 110, which are arranged at regular intervals, as an array. A diameter of the pillar 150a is, for example, 1 μm, and a gap between adjacent pillars is, for example, 0.5 μm.

Here, the bottom of the flow channel 120 is covered by an $SiO_2$ film 111, and the pillar array 150 is also formed of $SiO_2$. Further, an upper portion of the flow channel 120 is covered by a cap layer 115 formed of $SiO_2$. Ashing holes 116 for speedily removing a sacrifice layer for flow channel formation are formed at several places of the cap layer 115.

In the opening portion 142, a back opening 117 is provided at the back side of the flow channel 120, and a micropore 130 is provided at the bottom of the flow channel 120. The flow channel 120 and the back opening 17 of the Si substrate 10 are spatially connected to each other via the micropore 130.

In the first semiconductor micro-analysis chip, when a sample liquid is poured into an introduction opening 141, that is, an inlet, the sample liquid flows through the flow channel 120 and reaches a discharge opening 142, that is, an outlet by the capillary action. The back opening 117 is filled with an electrically conductive liquid which does not contain a particulate sample. Then, electrodes (formed of, for example, metal wires) for measuring the current passing through the micropore 130 are inserted into the outlet 142 and the back opening 117, and a voltage is applied to the electrodes by the voltage driving circuit 5 or the current driving circuit 6, thereby observing an ionic current flowing through the electrodes. When a particle passes through the micropore 130, the particle occupies a part of the micropore 130, and hence the electrical resistance of the portion of the micropore 130 changes. The ionic current is changed in accordance with the change in the electrical resistance. A fine particle, which has passed through the micropore 130, can be detected by observing the change in the ionic current when the particle passes through the micropore 130, using the current-voltage conversion circuit 2 and the analysis circuit 3.

The semiconductor micro-analysis chip as described above is made of a semiconductor wafer such as Si, and mass production technology with semiconductor fabrication process technology can be utilized. For this reason, the semiconductor micro-analysis chip can be miniaturized to a considerable degree and be manufactured in large quantities in comparison with a micro-analysis chip using a quartz substrate or a resin substrate that is often adopted in the prior art. Thus, a large number of semiconductor micro-analysis chips can be manufactured at low cost.

Further, the semiconductor micro-analysis chip does not require bonding process of bonding another substrate or a cover glass to form a sealing structure (lid) of the flow channel, and the cost of the bonding process can be cut down. Further, since the particles are to be detected electrically, noise separation from detection signals by utilizing electronic circuit technology, and highly-sensitive detection with real-time digital processing (statistical processing, etc. can be achieved. Moreover, a detection system can be made drastically compact in comparison with an optical detection system because the micro-analysis chip does not require equipment such as an optical system which occupies much space.

Also, a plurality of holes are provided in the small flow channel, and these holes are used as the ashing holes for removing the sacrifice layer formed for forming the flow channel. The time required for removing the sacrifice layer can be thereby reduced drastically, and the manufacturing cost can be reduced.

[Second Semiconductor Micro-Analysis Chip]

Figure 15:
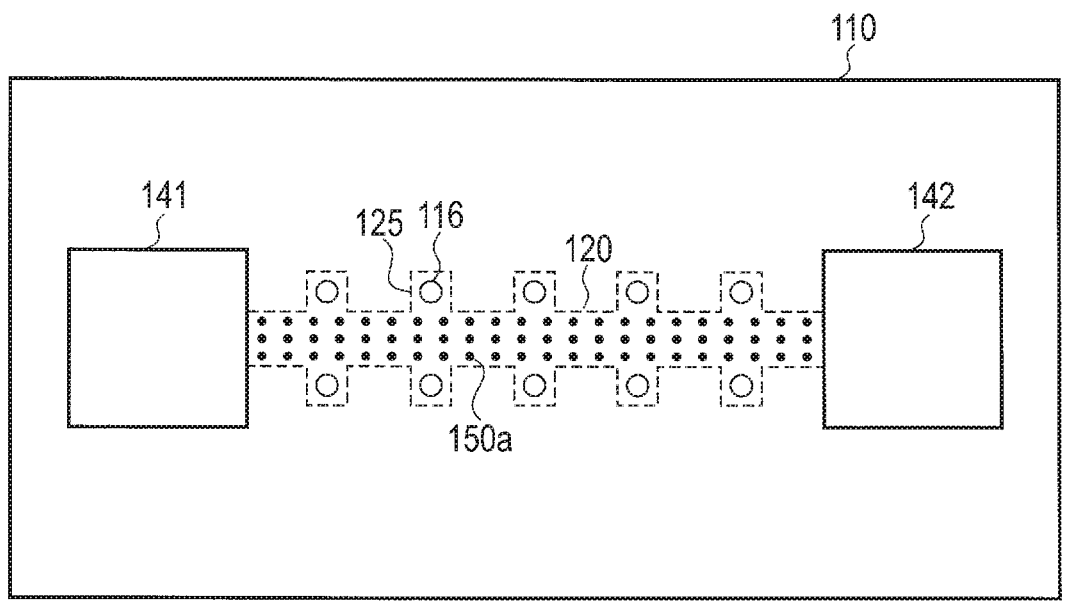
FIG. 15 is a schematic plan view showing the structure of a second semiconductor micro-analysis chip.

FIG. 15 is a plan view showing a brief structure of a second semiconductor micro-analysis chip. Note that structural elements identical to those in FIG. 13 will be denoted by the same reference numbers as in FIG. 13, and detailed explanations of them will be omitted.

The point in which the second semiconductor micro-analysis chip is different from the first semiconductor micro-analysis chip is that a channel portion 125 which communicates with a flow channel 120 is provided on a side part of the flow channel 120, and an ashing hole 116 is formed in a cap layer 115 above the channel portion 125. For example, on both side surfaces of the flow channel 120, channels portions 125 which are slightly larger than ashing holes to be formed are arranged at regular intervals, and the ashing holes 116 are formed in the channel portions 125, respectively.

Even in this structure, because the ashing holes 116 are provided, removal of a sacrifice layer in forming the flow channel 120 can be conducted speedily as in the first semiconductor micro-analysis chip. Further, the ashing holes 116 can be used as air holes for passing a sample liquid. Furthermore, holes are not directly formed in the flow channel 120, but the holes 116 are formed in the channel portions 125 provided at side walls of the flow channel. Accordingly, the semiconductor micro-analysis chip has an advantage of being able to form the holes 116 without decreasing the strength of a flow channel ceiling.

[Third Semiconductor Micro-Analysis Chip]

Figure 16:
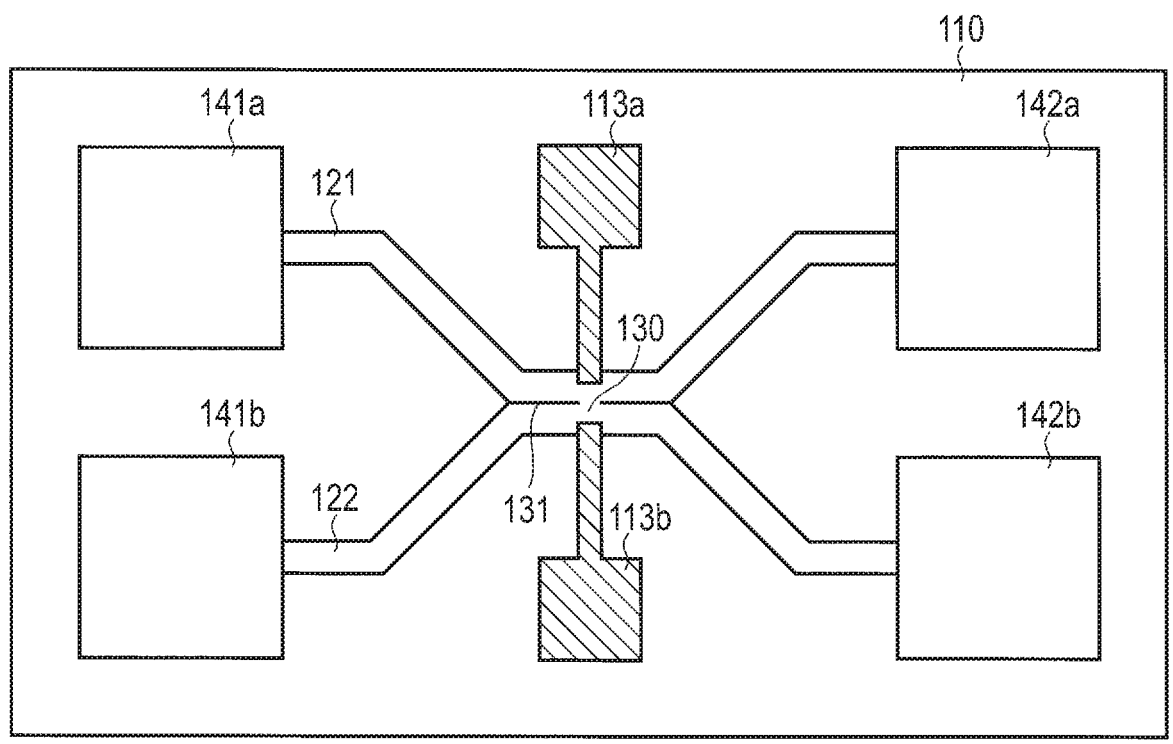
FIG. 16 is a schematic plan view showing the structure of a third semiconductor micro-analysis chip.

FIG. 16 is a plan view for schematically illustrating a third semiconductor micro-analysis chip, and FIG. 17 is a perspective view for explaining a on structure of the third semiconductor micro-analysis chip.

In the figures, reference number 110 denotes a semiconductor substrate formed of, for example, Si. Reference numbers 141a, 141b, 142a and 142b denote reservoirs into and out of which the sample liquid is injected and discharged. More specifically, reference number 141a denotes a sample liquid introduction region, reference number 141b denotes an electrolyte introduction region, reference number 142a denotes a sample liquid discharge region, and reference number 142b denotes an electrolyte discharge region. These reservoirs are formed by etching, using selective etching, the surface of the Si substrate 110 to, for example, a square pattern of 1 mm and a depth of 2 μm.

Reference number 121 denotes a first flow channel in which a sample liquid flows, and 122 denotes a second flow channel in which the sample liquid or an electrolyte flows. The flow channels 121 and 122 are arranged to be partially close to each other in different layouts, and are formed by, for example, etching the Si substrate 110 to a width of 50 μm and a depth of 2 μm. Further, an upper portion of each of the flow channels 121 and 122 is covered with an insulating thin film (having a thickness of, for example, 200 nm) such as a silicon oxide ($SiO_2$) film, a silicon nitride($SiN_x$) film, or an alumina ($Al_2O_3$) film. As shown in FIG. 17, flow channel caps (i.e., lids to seal the flow channels 121 and 122) as cap layers 115 are formed on the upper portions of the flow channels 121 and 122. Both the first and the second flow channels are thereby formed as groove-shaped tunnel flow channels. Further, in the cap layers 115, ashing holes to be used when removing a sacrifice layer may be formed.

At this time, the cap layers 115 are extended to the connections between the channels and the reservoirs 141a, 141b, 142a and 142b, so that the sample liquid or electrolyte can be introduced into the connections between the upper portions of the reservoirs and the channels. As a result, the channels 121 and 122 become tunnel-shaped channels that open to parts of the reservoirs.

Reference number 130 denotes a micropore provided at a contact portion between the first flow channel 121 and the second flow channel 122. The micropore 130 is formed by partial etching of a partition 131 (for example, an $SiO_2$ wall with a thickness of 0.2 μm) between the flow channel 121 and the flow channel 122 in a slit shape. The size (width) of the micropore 130 is not limited as long as it is slightly greater than the size of particles to be detected. When the size of the particles to be detected is 1 μm in diameter, the width of the micropore 130 of FIG. 16, may be, for example, 1.5 μm.

Reference numbers 113a and 113b denote electrodes configured to detect the particles. The electrodes 113a and 113b are formed to be partially exposed inside the flow channels 121 and 122, respectively. As the materials of the electrodes 113a and 113b, AgCl, Pt, Au, etc., may be used in the portion of surfaces where the electrodes are in contact with the sample liquid. The electrodes 113a and 113b do not necessarily have to be integrated as shown in FIG. 17. That is, even if the electrodes 113a and 113b are not integrated, the particles can be detected by attaching external electrodes to the inlets and outlets of the flow channels, respectively.

An ionic current flowing through the micropore 130 is basically determined on the basis of the aperture size of the micropore 130. In other words, a current (a steady current when the particles do not pass through the flow channels) caused to flow by applying a voltage to the electrodes 113a and 113b in the flow channels 121 and 122, which are filled with the electrolytes (solutions obtained by dissolving an electrolyte which allow passage of ionic currents), respectively, is determined on the basis of the aperture size of the micropore 130.

When a particle to be detected passes through the micropore 130, the particle partially blocks the passage of ions through the micropore 130, causing the ionic current reduction in accordance with the degree of blockage. However, if the particle is conductive or can become conductive at a surface level, an ionic current increase corresponding to the particle passage through the micropore 130 is observed because of electrical conduction of the particle itself caused by giving and receiving of ion charges. Such ionic current variation is determined on the basis of the relative relationships in shape, size, length, etc., between the micropore 130 and the particles. For this reason, a feature of the particles passing through the micropore can be recognized by observing the amount of variation, transient variation, etc., of the ionic current.

The aperture size of the micropore 130 may be determined by considering ease of passage of the particles to be detected and variation degree (sensitivity) of the ionic current. For example, the aperture size of the micropore 130 may be 1.5 times to 5 times as great as the outside diameter of the particles to be detected. As the electrolyte to disperse the particles to be detected, a KCl solution or various buffer solutions such as a Tris Ethylene diamine tetra acetic acid (TE) buffer solution and a phosphate buffered saline (PBS) may be used.

In the third semiconductor micro-analysis chip shown in FIGS. 16 and 17, for example, the first flow channel 121 is used as a sample liquid introduction flow channel, and the sample liquid (i.e., a suspension liquid obtained by dispersing fine particles to be detected in an electrolyte) is dropped to the reservoir 141*a* or 142*a*. At this time, since the flow channel 121 is the tunnel-like flow channel as described above, as soon as the sample liquid reaches the entrance of the flow channel 121, the sample liquid is drawn into the flow channel 121 by the capillary action, and then the interior of the flow channel 121 is filled with the sample liquid. Here, if the ashing holes are formed, they serve as air holes, and the filling of the sample liquid can be carried out smoothly.

The second flow channel 122 is used as a flow channel for receiving the detected particles. An electrolyte which does not include the particles to be detected is dropped into the reservoir 141*b* or 142*b*, and then the interior of the reservoir 141*b* or 142*b* is filled with the electrolyte. In the above state, by applying a voltage across the electrode 113*a* and the electrode 113*b* from the voltage driving circuit 5 or the current driving circuit 6, particles passing through the micropore 130 can be detected.

A polarity of the voltage applied across the electrodes 113*a* and 113*b* varies depending on the charge of the particles (bacteria, viruses, labeled particles, etc.) to be detected. For example, to detect negatively-charged particles, a negative voltage is applied to the electrode 113*a*, and a positive voltage to the electrode 113*b*. In this configuration, the particles are electrophoresed by the electric field in the solution, and then the ionic current variation is observed according to above-mentioned mechanism.

The second flow channel 122 as well as the first flow channel 121 can be filled with the sample liquid. This condition can be employed particularly when the charge of the particles to be detected is unclear or when positively-charged particles and negatively-charged particles are mixed. Even when the charge of the particles to be detected is known, the detection may be executed by filling both the flow channels with the sample liquid. In this case, because two types of solutions, i.e., the sample liquid and the electrolyte, do not need to be prepared, an operation relevant to detection of the particles can be simplified. However, the reservoirs (141*a* and 141*b*, 142*a* and 142*b*) of the flow channels need to be electrically separated from each other, i.e., the sample liquid in one of the reservoirs needs to be separated from that in the other one.

Thus, in the third semiconductor micro-analysis chip, the particles can be detected only by the sample liquid introduction and the electrical observation. Further, the ultraminiaturization and mass production can be implemented by the semiconductor processing technique, and a particle detection circuit, a particle discrimination circuit, etc., can also be integrated. Accordingly, ultraminiaturized and highly-sensitive semiconductor micro-analysis chips can be manufactured in large quantities and at low cost.

Therefore, highly-sensitive detection of bacteria, viruses, etc., can be easily conducted. The semiconductor micro-analysis chip as described can contribute to preventing epidemic diseases from spreading and maintaining food safety, by applying the semiconductor micro-analysis chip to a rapid test of infectious pathogens, food-poisoning-causing bacteria, etc. The semiconductor micro-analysis chips as described are suitable for use in situations where a large number of chips need to be provided at very low cost. For example, they may be suitably used as high-speed primary test kits for diseases which require emergency quarantine action such as new strains of influenza, simple home-administered food-poisoning tests, and the like.

[Fourth Semiconductor Micro-Analysis Chip]

Figure 18:
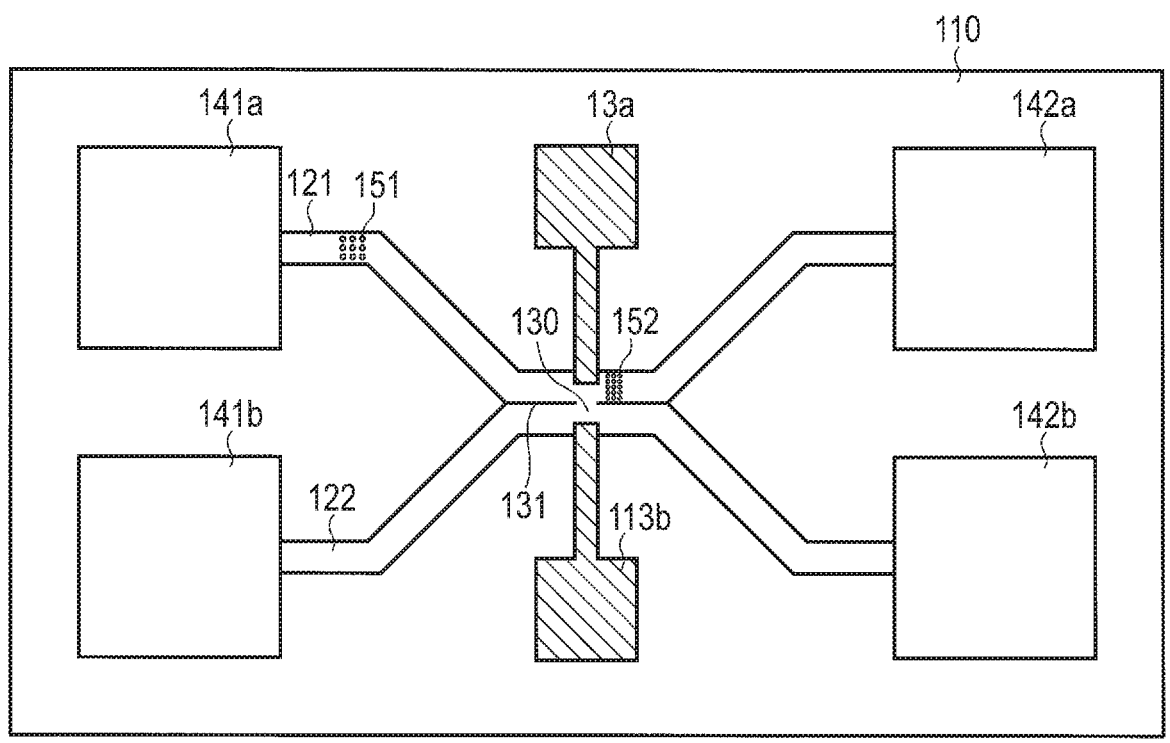
FIG. 18 is a schematic plan view showing the structure of a fourth semiconductor micro-analysis chip.

FIGS. 18 and 19 illustrate a brief structure of a fourth semiconductor micro-analysis chip. FIG. 18 is a plan view of the semiconductor micro-analysis chip, and FIG. 19 is a perspective view of the same. In the semiconductor micro-analysis chip, a particle size filter is provided in a sample liquid flow channel 121.

In FIGS. 18 and 19, reference numbers 151 and 152 denote micro-size pillar arrays composed of micro-columnar structures (pillars) arranged at regular intervals to filter the particles in a sample liquid by size based on the intervals. Wall-like structure (slit) arrays, etc., can also be used instead of the pillar arrays 151 and 152. A structure and a function of the particle filter will be described taking the case of introducing the sample liquid to a reservoir 141*a* and guiding the sample liquid to the flow channel 121 as an example.

Figure 20:
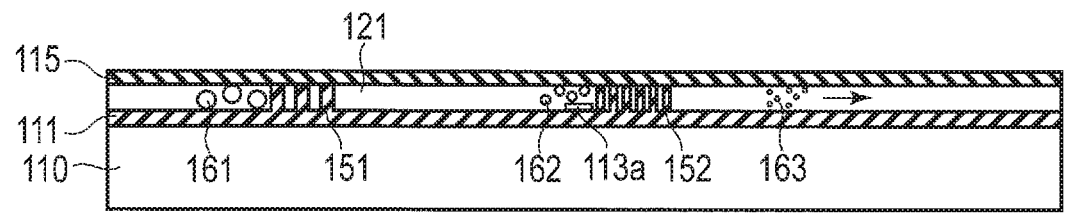
FIG. 20 is a cross-sectional view conceptually showing the function of a pillar array in the fourth semiconductor micro-analysis chip.

FIG. 20 schematically illustrates the function of the pillar arrays 151 and 152. The first pillar array 151 is provided at an upstream side of a micropore 130, and serves as a filter configured to remove large particles 161 which would clog the micropore 130. The pillar array 151 is formed such that pillars are provided at intervals which allow particles-to-be-detected 162 to pass through the pillar array 151 but do not allow the particles 161 having a diameter larger than the aperture of the micropore 130 to pass through. For example, if the diameter of the particle to be detected is 1 µm, and the diameter of the micropore is 1.5 µm, the pillars of the pillar array 151 are arranged in a manner described below. That is, as the pillar array 151, columnar structures having a diameter of 2 µm or quadrangular prism-shaped structures having a length of 2 µm on a side are formed so as to have an interval of, for example, 1.3 µm at maximum in a transverse direction of the flow channel. The number of steps (i.e., the number of rows) of the pillars of the pillar array 151 may be determined in consideration of trap efficiency of the large particles 161. Substantially all the particles having an outer diameter of 1.3 µm or more can be trapped when the pillar array 151 is arranged in the transverse direction of the flow channel with, for example, ten steps (ten rows) of pillars.

In addition, a multi-stepped filter structure can be provided such that a pillar array (not shown) having greater intervals of pillars is provided in the upstream of the pillar array 151 to preliminarily filter the particles having a diameter of, for example, 5 µm or more before the pillar array 151. In this case, it becomes easy to prevent the particle filter (pillar array 151) itself from being clogged by the large particles 161. For this reason, pretreatments such as centrifugation and preprocessing filtration of the sample liquid can be omitted, and thus the work for detecting the particles can be simplified and accelerated.

In FIG. 20, the pillar array 152 serves as a collector configured to collect and concentrate the particles-to-be-detected 162. The pillar array 152 is provided at a downstream side of the micropore 30, and pillars of the pillar array 152 are formed at intervals which do not allow the particles-to-be-detected 162 to pass through, but allow the electrolyte and microparticles 163 that are out of the scope of detection to pass through. For example, if the diameter of the particles to be detected is 1 µm, as the pillar array 152, columnar structures having a diameter of 1 µm or quadrangular prism-shaped structures having a length of 1 µm on a side are formed so as to have an interval of, for example, 0.9 µm at maximum in the transverse direction of the flow channel. The number of steps (i.e., the number of rows) of the pillars of the pillar array 152 may be determined in consideration of trap efficiency of the particles-to-be detected 162. Substantially all the particles having an outer diameter of 1.0 µm or more can be trapped by providing the pillar array 152 in the transverse direction of the flow channel 21 with, for example, ten steps (ten rows) of pillars.

Figure 21A:
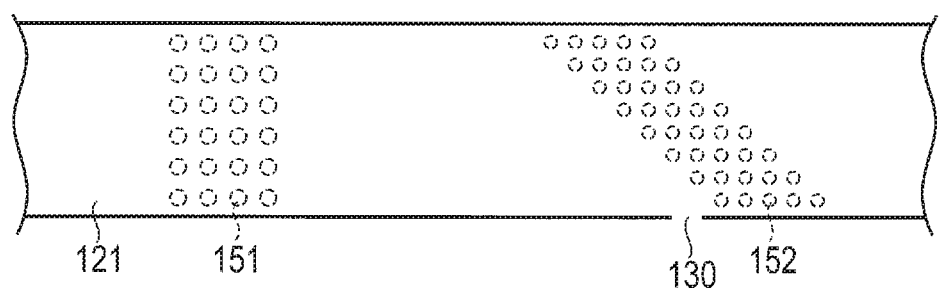
FIGS. 21A and 21B show a pillar array example in the fourth semiconductor micro-analysis chip.
Figure 21B:
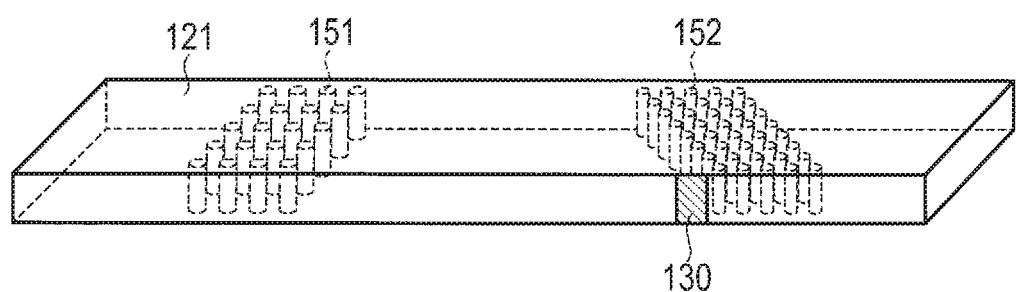

In addition, as shown in FIGS. 21A and 21B, pillars of the pillar array 152 may be arranged so as to obliquely cross the flow channel 121, with the micropore 130 positioned close to a portion located at the most downstream side of the upstream side ends of the pillars. Since the trapped particles are guided to the portion of the micropore 130 efficiently, the detection efficiency can be enhanced.

Only one of the pillar arrays 151 and 152 may be provided instead of providing both of the pillar arrays. The number of the pillar arrays to be provided can be determined in consideration of the features of the sample liquid to be applied, process of the detection steps, etc. In addition to the pillar arrays 151 and 152 which serve as the particle size filters, pillar arrays with intervals greater than the intervals of the pillar arrays 151 and 152 may be formed all over the flow channel. In this case, each of the pillars can function as a supporting column of the cap of the flow channel, and can prevent the flow channel cap from being collapsed by an external pressure or a surface tension of the sample liquid. Moreover, the surface tension of the electrolyte can also act between the pillars to work as a driving force to draw the electrolyte, thereby enabling the flow channel to be filled with the sample liquid and the electrolyte more easily.

Pillar arrays may also be formed at intervals greater than the pillar intervals which can be the particle size filter, in the regions of the reservoirs 141a, 141b, 142a and 142b with no flow channel can provided. With the above configuration, the sample liquid and the electrolyte dropped onto the inlets can be spread by the surface tension of the pillar arrays, and the solutions can smoothly flow into the flow channels.

As can be seen, in the fourth semiconductor micro-analysis chip, the particle size filtering function can be added by arranging the pillar arrays (or slit arrays) in the sample liquid inlet flow channel. Further, the detection steps can be simplified and the accuracy in detecting the particles can be enhanced by adding the functions of removing unnecessary particles, concentrating the particles to be detected, etc. Therefore, not only the advantage similar to the advantage of the third semiconductor micro-analysis chip can be obtained, but the present semiconductor micro-analysis chip also has the advantage that the detection time can be reduced and the detection errors can be reduced and prevented.

[Fifth Semiconductor Micro-Analysis Chip]

FIG. 22 is a perspective view showing a brief structure of a fifth semiconductor micro-analysis chip. In this chip, flow channels 121 and 122 are not constituted by grooves of an Si substrate 110, but covered with tunnel-like insulating films. That is, instead of using engraved grooves of the Si substrate 110 as the flow channels, insulating film tunnel type flow channels, which are made by forming a sacrifice layer in a flow channel pattern, and then covering an upper surface and side surfaces or the sacrifice layer by an insulating film, are used.

Since the present semiconductor micro-analysis chip does not involve etch-back process or CMP process of the sacrifice layer, in-plane unevenness such as residues of the sacrifice layer and reduction of film thickness hardly occurs. Hence, process failure in the sacrifice layer formation steps is considerably reduced. Accordingly, not only the advantage similar to that of the third semiconductor micro-analysis chip can be obtained, a manufacturing yield can also be improved. Further, if ashing holes are formed, the time required for the ashing process can be reduced and equalized. In addition, a gap between a thermally-oxidized film 11 and a cap layer 15 which would be caused by the residues of the sacrifice layer is essentially hard to be created. For this reason, a problem of leakage failure of an ionic current is also substantially resolved.

The reservoirs (141a, 141b, 142a, and 142b) of the present inspection chip can be basically formed similarly to those shown in FIGS. 17 and 20, but liquid dams of the reservoirs need to be formed at portions of connection between the flow channels of the insulating film tunnel type and the reservoirs. For this reason, Si terraces may be formed beside the openings at the ends of the flow channels 121 and 122, as shown in FIG. 22, or dummy flow channels may be formed at up to the Si terrace portions beside the openings at the ends of the flow channels, and used as the liquid dams.

[Sixth Semiconductor Micro-Analysis Chip]

Figure 23:
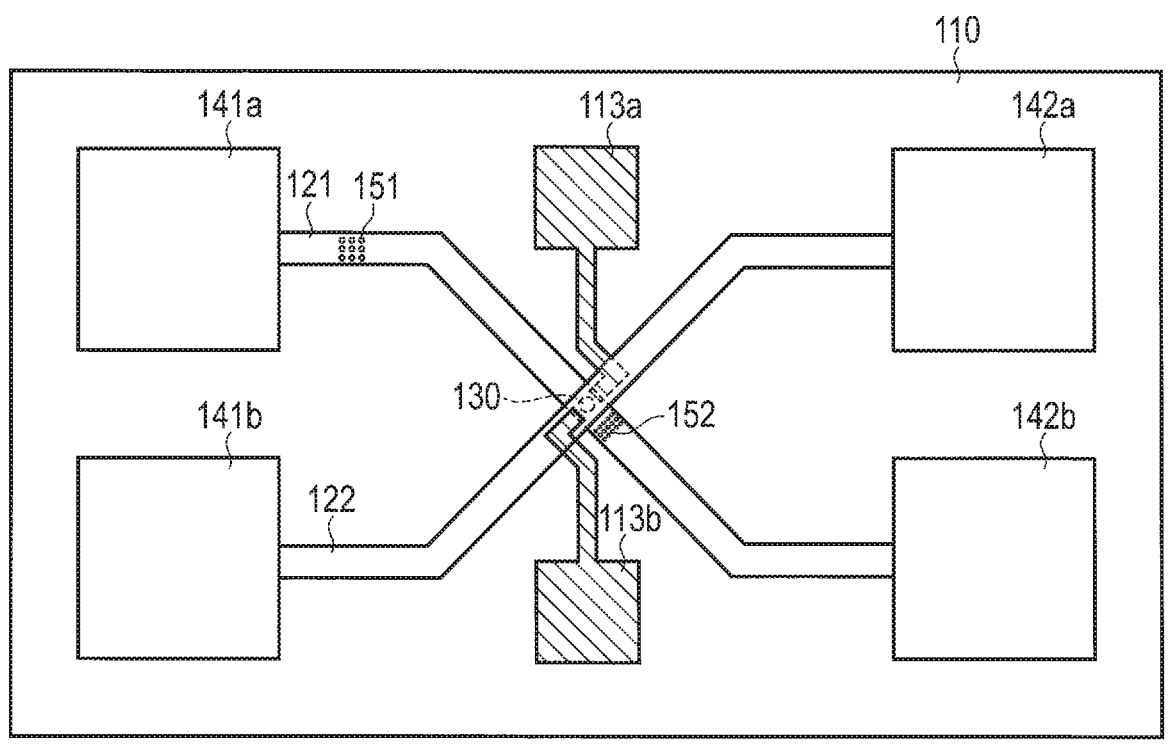
FIG. 23 is a schematic plan view showing the structure of a sixth semiconductor micro-analysis chip.

FIG. 23 is a plan view showing a brief structure of a sixth semiconductor micro-analysis chip. In this chip, a flow channel 121 and a flow channel 122 are formed in different steps, and a piled portion (contact portion) where the two flow channels intersect each other is provided. By this structure, double-decker flow channels in which the flow channel 121 serving as a sample supplying flow channel is formed at a lower side, and the flow channel 122 serving as a sample receiving flow channel is formed at an upper side are provided. Here, a micropore 130 is provided at the piled portion (contact portion) of the two flow channels. In other words, the micropore 130 is formed by photolithography at a partition (i.e., a cap layer 115 of the first flow channel 121) serving as an upper surface of the first flow channel 121 and a lower surface of the second flow channel 122.

In the semiconductor micro-analysis chip shown in FIGS. 16 to 23, the micropore 130 needs to be formed at the partition perpendicular to the silicon substrate 10 since two flow channels are laterally adjacent to each other with the partition sandwiched between them. For this reason, the slit-like micropore 130 is formed by patterning the partition from the side portions. At this time, the shape of the micropore is a rectangle close to a square when a depth of the flow channels is the same as a width of the micropore. Alternatively, the micropore is a vertically long slit when the depth of the flow channels is greater than the width of the micropore. For this reason, when particles pass through the micropore 130, the aperture of the micropore 30 cannot be sufficiently shielded by the particles, and thus a variation in an ionic current is small in comparison with a circular micropore.

In contrast, in the analysis chip shown in FIG. 23, the micropore 130 can be directly patterned, and the aperture shape of the micropore can be arbitrarily determined. Thus, the micropore 130 can be designed to have a circular aperture by which the ion conduction can be most effectively shielded with the particles. At this time, the variation in the ionic current associated with passing of the particles to be detected through the micropore 130 can be maximized, and the particles can be detected with much higher sensitivity than the detection by the semiconductor micro-analysis chip shown in FIGS. 16 to 22.

FIG. 24 illustrates a specific example of the double-decker flow channels. In this example, the first flow channel 121 is a tunnel flow channel of an Si substrate engraving type similar to the flow channel shown in FIG. 17 while the second flow channel 122 is a flow channel of an insulating film tunnel type similar to the flow channel shown in FIG. 22.

Figure 25A:
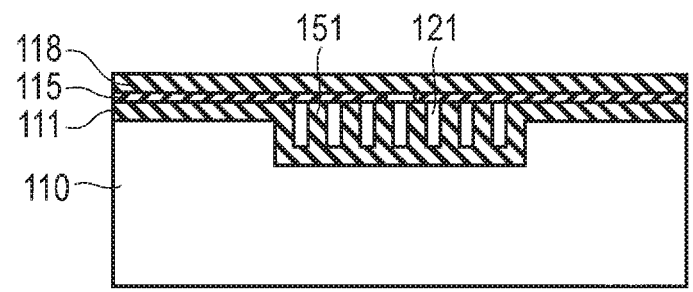
FIGS. 25A to 25C are schematic cross-sectional views showing the structure of the sixth semiconductor micro-analysis chip.
Figure 25B:
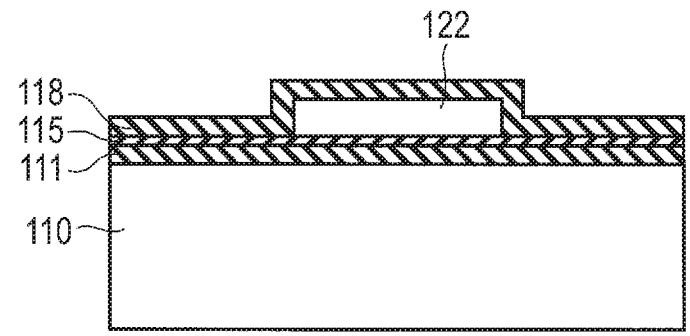

The first flow channel 121 is a tunnel flow channel of an engraving type as shown in FIG. 25A, and the second flow channel 122 is a flow channel of an insulating film tunnel type, that is, a flow channel made of an insulating film (a cap layer) 118, as shown in FIG. 25B.

Figure 25C:
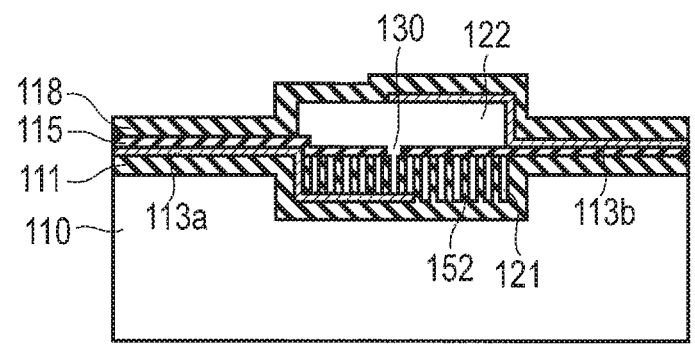

In addition, the micropore 130 is formed in the insulating film 15 at the contact portion where the two flow channels 21 and 22 intersect each other, as shown in FIG. 25C, and an aperture shape of the micropore can be determined arbitrarily. The electrodes for observing the ionic current are formed on a lower surface of the first flow channel 121 and an upper surface of the second flow channel 122, respectively. High sensitivity can be thereby realized by optimizing the shape of the micropore. In addition, the present semiconductor micro-analysis chip comprises the tunnel flow channel 121 of the Si engraving type, and the second flow channel 122 is formed on the insulating film 115. Therefore, the semiconductor micro-analysis chip also has an advantage that even if a gap is formed between an insulating film 111 and the insulating film 115 due to the residues of the sacrifice layer, no leakage current occurs between the two flow channels.

Since the two flow channels are arranged to intersect each other, a sample liquid introduced into a reservoir 141a is to be discharged into a reservoir 142b. However, this structure may be modified as shown in the plan view of FIG. 26 or in the perspective view of FIG. 27, so that the two flow channels are stacked, and each of the channels is bent in the stacked position to permit, for example, the sample liquid introduced in the reservoir 141a to be discharged to the reservoir 142a (similarly, to permit the sample liquid introduced in the reservoir 141b to be discharged to the reservoir 142b).

Figure 28A:
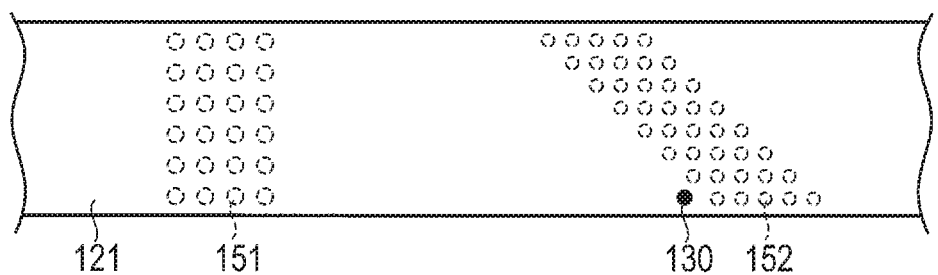
FIGS. 28A to 28D show pillar array examples in the sixth semiconductor micro-analysis chip.
Figure 28B:
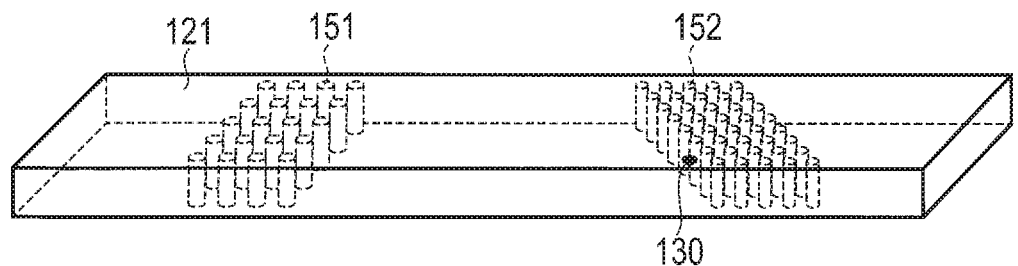

In FIGS. 28A and 28B, a pillar array 152 is arranged such that pillars of the pillar array 152 obliquely cross the flow channel 21, and the micropore 130 is positioned near a portion at the most downstream side of the upstream side ends of the pillars. FIG. 28A is a plan view, and FIG. 28B is a perspective view. Thus, detection efficiency can be enhanced since the articles trapped by the pillar array 152 are efficiently guided to the micropore 130.

Figure 28C:
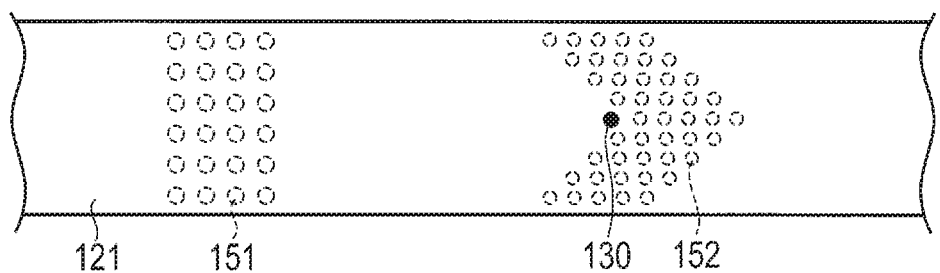
Figure 28D:
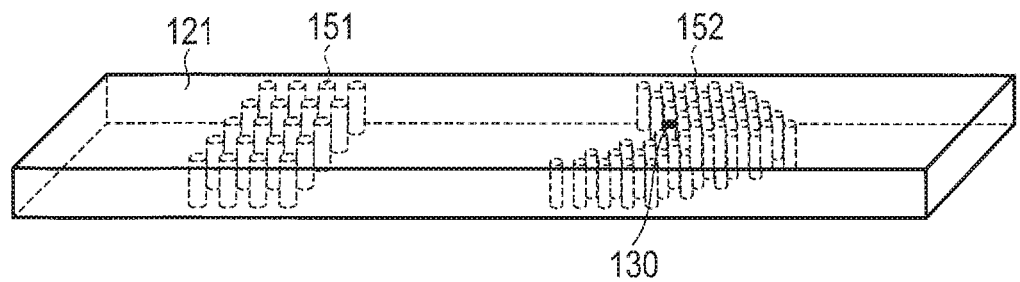

Further, in FIGS. 28C and 28D, pillars of the pillar array 152 are arranged in a form of ">" with respect to the flow channel direction. FIG. 28C is a plan view, and FIG. 28D is a perspective view. The same advantage as that of the arrangement shown in FIGS. 21A and 21B can be obtained by arranging the pillar array as such. Considering that the micropore 130 is formed in a predetermined size, the micropore 130 is positioned at a central portion of the flow channel 121, when the pillars are arranged in the form of ">". Accordingly, the arrangement in the form ">" shown in FIGS. 28C and 28D can be formed more easily than the oblique arrangement shown in FIGS. 28A and 28B.

Figure 29:
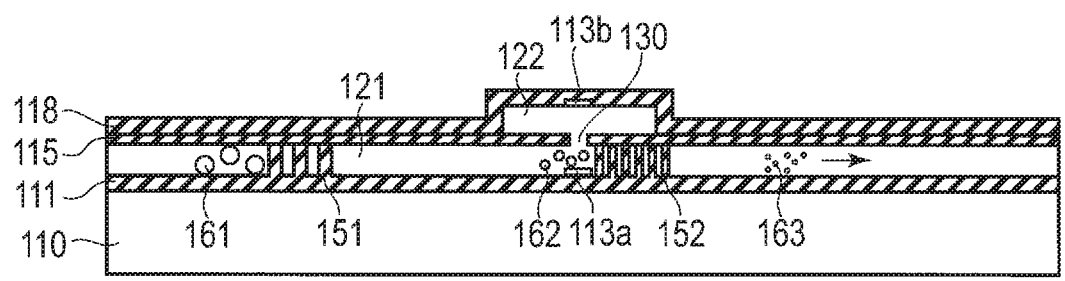
FIG. 29 is a cross-sectional view for explaining a particle detection mechanism in the sixth semiconductor micro-analysis chip.

FIG. 29 schematically shows a particle detection mechanism. A function of the pillar arrays 151 and 152 is the same as that as shown in FIG. 20. In FIG. 29, by applying a voltage between the electrodes 113a and 113b, particles 162 collected by the pillar array 152 are electrophoresed between the electrodes 113a and 113b, and moved to the side of the flow channel 122 through the micropore 130. At this time, since the ionic current flowing between the electrodes 113a and 113b varies, the particles 162 can be detected.

As can be seen, since the micropore 130 is formed to have the circular aperture by having the first flow channel 121 and the second flow channel 122 stacked, not only the same advantage as that of the third semiconductor micro-analysis chip can be obtained, but also the particles can be detected, with higher sensitivity.

(Seventh Semiconductor Micro-Analysis Chip)

FIG. 20 is a perspective view showing a brief structure of a seventh semiconductor micro-analysis chip. This chip is a modified case in which a flow channel 121 and a flow channel 122 are formed in different steps, and a piled portion (contact portion) of the two flow channels is provided.

Both the first flow channel 121, which is a sample inlet flow channel, and the second flow channel 122, which is a sample receiving flow channel, are insulating film tunnel type flow channels. The two flow channels are formed in different steps, and a micropore 130 is formed by photolithography, at the piled portion of the two flow channels.

The inspection chip has a feature of solving inconvenience that filling the second flow channel with a sample liquid or an electrolyte sometimes cannot be successfully executed for the reason that the second flow channel 122 is different in height from a junction between the second flow channel 122 and the reservoirs (i.e., an opening portion) in the inspection chip in FIG. 29. In the present chip, the first flow channel 121 of an insulating film tunnel type is formed in a flow channel portion 110a formed on a substrate, and the second flow channel 122 of an insulating film tunnel type is formed similarly after the first flow channel 121 has been formed. Thereby, the first flow channel 121 and the second flow channel 122 can be substantially the same height at their reservoir portions.

At the piled portion (i.e., the contact portion in FIG. 30) of the two channels, a space of the second flow channel 122 can be secured as shown in FIG. 29, because in the process of forming the second flow channel, a sacrifice layer for the second flow channel automatically climbs over the first flow channel 121. In the case of filling the first flow channel 121 and the second flow channel 122 with the sample liquid (or electrolyte), a problem that filling failure occurs at either of the flow channels can be thereby solved.

Thus, the present chip has an advantage of being able to prevent, failure in filling the flow channels with the sample liquid or the electrolyte, in addition to the advantage of the sixth semiconductor micro-analysis chip.

[Eighth Semiconductor Micro-Analysis Chip]

Figure 31:
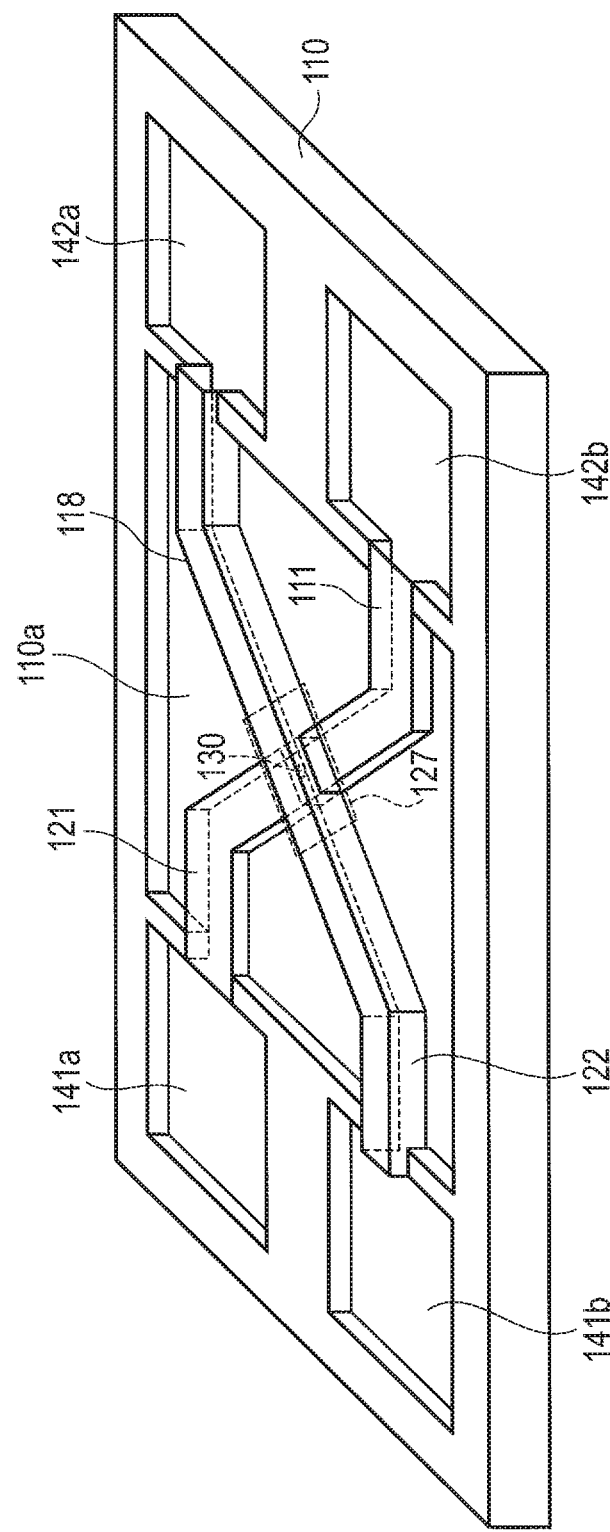
FIG. 31 is a schematic perspective view showing the structure of an eighth semiconductor micro-analysis chip.

FIG. 31 is a perspective view showing a brief structure of an eighth semiconductor micro-analysis chip. This chip is a modified case in which a flow channel 121 and a flow channel 122 are formed in different steps, and a piled portion (contact portion) or the two channels is provided. FIG. 32A is a cross-sectional view of the flow channels, and FIG. 32B is a cross-sectional view of the contact portion of the flow channels, Similarly to the inspection chip shown in FIG. 30, both the first flow channel 121, which is a sample inlet flow channel, and the second flow channel 122, which is a sample receiving flow channel, are insulating film tunnel type flow channels. The two flow channels are formed in different steps, and a micropore 130 is formed by photolithography at the piled portion of the two flow channels. Further, the second flow channel 122 is formed to be higher than the first flow channel 121, as shown in FIGS. 32A and 32B.

Space above the first flow channel, which works as the second flow channel 122, can be secured with certainty at the piled portion (contact portion of FIG. 31) of the flow channels 121 and 122. Thus, a problem that the second flow channel 122 is crushed at the piled portion of the flow channels 121 and 122, which may sometimes arise in the semiconductor micro-analysis chip shown in FIG. 30, can be resolved. In the inspection chip shown in FIG. 30, the second flow channel 122 is formed in the expectation that a second sacrifice layer would naturally climb over the first flow channel. However, because of product variations in the sacrifice layer materials and fluctuations of the temperature or moisture in the processing environment, it is difficult to form the flow channels with guaranteed reproducibility. In the semiconductor micro-analysis chip shown in FIG. 31, expecting an upper surface of the second flow channel to naturally climb over the first flow channel is not needed, because the flow channels which have different heights can be formed with certainty under different conditions for coating the sacrifice layer (i.e., spin speed, etc.) or using the sacrifice layer materials of different viscosity.

At this time, it is desirable that the first flow channel 121 and the second flow channel 122 are formed to have the same cross-sectional area to equalize the amounts of sample liquid (or electrolyte) filled into the flow channels 121 and 122, which causes a substantially equal capillary action in the flow channels 121 and 122. For example, in the case where the first flow channel 121 has a width of 50 μm and a height of 2 μm, and the second flow channel has a width of 20 μm and a height of 5 μm, the flow channels 121 and 122 have the same cross-sectional area and 3 μm-height space between the first flow channel and the second flow channel can be secured at the piled portion.

The present chip therefore has an advantage of being able to solve the problem of the piled portion of the flow channels 121 and 122 being crushed and to implement the micro-analysis chip of higher reliability, in addition to the advantage of the seventh semiconductor micro-analysis chip.

[Ninth Semiconductor Micro-Analysis Chip]

FIG. 33 is a perspective view showing a brief structure of a ninth semiconductor micro-analysis chip.

The basic structure of this chip is similar to that of the eighth semiconductor micro-analysis chip previously described. A difference between the present chip and the eighth semiconductor micro-analysis chip is that instead of providing ashing holes in flow channels, channel portions for forming ashing holes are provided on side walls of the flow channels and ashing holes are provided on these channels portions.

That is, at several portions of flow channels 121 and 1122, channel portions 125 which are the same in height as the flow channels are provided on the side walls, and ashing holes 116 are formed on the upper surfaces of the channel portions 125. Further, pillar arrays which are not shown are formed in the flow channel 121.

With such a structure, in the process of removing a sacrifice layer for flow channel formation, oxygen plasma can be introduced into the flow channels 121 and 122 from ends of the flow channels 121 and 122 and the ashing holes 116 of the channel portions 125. Thereby, the sacrifice layer removal can be carried out speedily.

Thus, an advantage similar to that of the eighth semiconductor micro-analysis chip can be obtained. Also, since the holes 116 are formed in the channel portions 125 provided on the side walls of the flow channels 121 and 122, instead of forming the holes directly in the flow channels 121 and 122, an advantage similar to that of the second semiconductor micro-analysis chip previously described can be obtained. [Tenth Semiconductor Micro-Analysis Chip]

FIG. 34 is a plan view showing a brief structure of a tenth semiconductor micro-analysis chip. In the following description, a sample liquid is introduced into both a flow channel 121 and a flow channel 122, but an electrolyte may be introduced into either of the flow channels instead of the sample liquid.

An absorber 171a which can absorb the sample liquid is arranged on a reservoir 141a, and an absorber 171b which can absorb the sample liquid or the electrolyte is arranged on a reservoir 141b. Further, an absorber 172a which can absorb the sample liquid is arranged on a reservoir 142a, and an absorber 172b which can absorb the sample, liquid or the electrolyte is arranged on a reservoir 142b. As the absorbers, filter paper and fiber assembly such as unwoven fabric can be used. Each of the absorbers may be arranged to cover all over a corresponding reservoir or arranged to partially cover the corresponding reservoir. However, the absorbers of adjacent reservoirs need to be separated from each other.

As described above in the third semiconductor micro-analysis chip, the sample liquid is supplied to the reservoir 141a and either one of the sample liquid and the electrolyte may be supplied to the reservoir 141b. An example of supplying the sample liquid to the reservoir 141b will be hereinafter described.

In this structure, the sample liquids including particles to be detected dropped on the absorbers 171a and 171b seep from the absorbers 171a and 171b and are guided into the reservoirs 141a and 141b. The sample liquids guided into the reservoirs 141a and 141b reach the reservoirs 142a and 142b through the flow channels 121 and 122, respectively. The sample liquids flowing through the flow channels 121 and 122 are absorbed into the absorbers 172a and 172b arranged on the reservoirs 142a and 142b. Once the absorbers 172a and 172b start absorbing the sample liquids in the reservoirs 142a and 142b, sample liquids flowing into the reservoirs 142a and 142b in succession are absorbed into the absorbers 172a and 172b. Thus, the sample liquids in the flow channels 121 and 122 flow continuously.

That is, by absorbing the sample liquids using the absorbers 172a and 172b, the sample liquids in the flow channels 121 and 122 can be made to flow without using electrophoresis or an external pump, and particles included in the sample liquids can be made to move in the flow of the sample liquids. For this reason, the absorbers 171a and 171b on the sides of the reservoirs 141a and 141b can be omitted.

In addition, a sufficient amount of sample liquid can be supplied to the flow channels 121 and 122 without increasing the size of the semiconductor micro-analysis chip, by arranging the absorbers 171a and 171b on the sample liquid inlet side. In general, introduction of the sample liquid into a micro-analysis chip is executed by using a micropipet, etc., and the amount of instillation of the sample liquid is approximately 10 to 10,000 μl. To contain this amount of sample liquid, for example, an area of approximately 100 mm² is required with a depth of 100 μm. Integrating such a large containing region results in the manufacture of a semiconductor micro-analysis chip much larger than required for integrating a functional part of an analysis chip, considerably increasing manufacturing cost. In addition, concentration of the particles in the sample liquid is generally low. If it is necessary to detect a number of fine particles, a large amount of sample liquid needs to be introduced into the chip, and thus the sample liquid containing region needs to be vast.

In the tenth semiconductor micro-analysis chip, sufficiently large absorbers 171a and 171b are provided outside the analysis chip, instead of integrating a very large sample liquid containing region. Then, the sample liquids are instilled into the absorbers 171a and 171b and introduced into the flow channels 121 and 122, respectively. The sample liquids discharged from a sample outlet side can be absorbed into the absorbers 172a and 172b. Thus, a larger amount of sample liquid than the amount of the sample liquid contained in the analysis chip can be introduced and discharged.

It is desirable that pillar arrays with intervals greater than those of the above-mentioned particle size filter be formed in regions of the reservoirs 141a, 141b, 142a, and 142b, and that the absorbers be arranged to contact the pillar arrays. In this way, delivery of the sample liquid or the electrolyte between the absorbers 171a, 171b, 172a and 172b and the corresponding inlets and outlets is smoothly executed by a surface tension of the pillar arrays. Further, the sample liquid or the electrolyte can easily and smoothly be introduced into the flow channel from the absorber.

Thus, not only the advantage similar to that of the first semiconductor micro-analysis chip can be obtained, but also the advantage described below can be obtained as a result of providing the absorbers 171a, 171b, 172a, and 172b on the reservoirs 141a, 141b, 142a, and 142b.

That is, the sample liquids in the flow channels 121 and 122 can be made to flow without using electrophoresis or an external pump, by providing the absorbers 172a and 172b on the sample liquid discharge region 142a, 142b side. Further, a sufficient amount of sample liquid can be supplied to the flow channels 121 and 122 without increasing the size of the semiconductor micro-analysis chip, by providing the absorbers 171a and 171b on the sample liquid introduction region 141a, 141b side. A large amount of sample liquid can therefore be handled by a very small analysis chip. In other words, cost can be considerably reduced by integrating functional parts of the semiconductor micro-analysis chip in a minimum area.

[Eleventh Semiconductor Micro-Analysis Chip]

Figure 35:
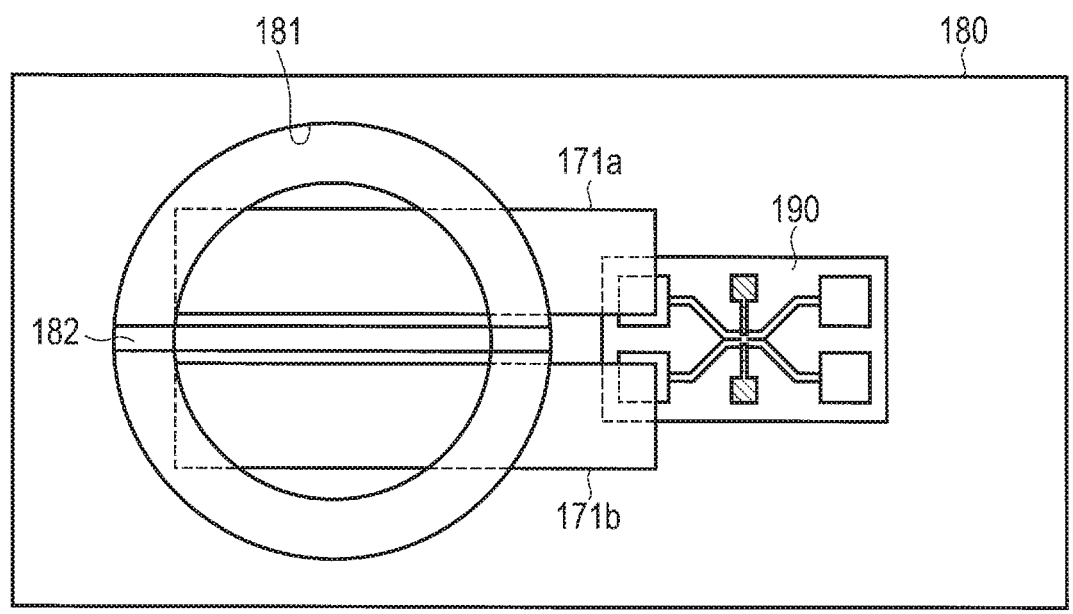
FIG. 35 is a schematic plan view showing the structure of an eleventh semiconductor micro-analysis chip.

FIGS. 35 and 36 show a brief structure of an eleventh semiconductor micro-analysis chip 190. FIG. 35 is a plan view and FIG. 36 is a perspective view.

In the present semiconductor micro-analysis chip, a sample liquid inlet port 181 is provided on a package 180 configured to contain the semiconductor micro-analysis chip shown in FIG. 33. The sample liquid inlet port 181 is formed by forming an aperture on a top surface located above absorbers 171a and 171b of the package 180, and providing a funnel-shaped solution guide configured to guide a sample liquid to the absorbers 171a and 171b. The sample liquid inlet port 181 is great enough to spread over both the absorbers 171a and 171b. A partition plate 182 configured to separate the sample liquid for the absorber 171a and the absorber 171b is provided in the sample liquid inlet port 181.

FIG. 36 does not illustrate absorbers 172a and 172b on a sample liquid outlet side, but of course, the absorbers 172a and 172b may be provided. In addition, the structure of the semiconductor micro-analysis chip 190 is not limited to the example shown in FIG. 33, but can be arbitrarily modified similarly to the above-described examples.

In this structure, the sample liquid can be absorbed into the absorbers 171a and 171b with certain separation, only by dripping the sample liquid onto a central portion of the sample liquid inlet port 181. Then, the sample liquid can be guided to reservoirs 141a and 141b corresponding to the absorbers 171a and 171b, respectively, and can be made to further flow into flow channels 121 and 122. Therefore, the sample liquid does not need to be introduced to the reservoirs 141a and 141b individually, and can be guided by a simple operation. In addition, the size of the micro-analysis chip, in particular, the size of the reservoir portions can be minimized enough to overlap the absorbers, and the micro-analysis chip can be ultra-miniaturized. As a result, the cost of the micro-analysis chip can be reduced.

(Modified Embodiments)

The particle inspection unit and the particle inspection system are not limited to the above-described embodiments.

In the embodiment, mainly the Si substrate is used as the inspection chip. However, the material of the substrate is not limited to Si, and other semiconductor substrate materials can be used as long as The semiconductor substrate can be processed in a general semiconductor manufacturing process. In addition, the insulating film is mainly expressed as a dielectric ($SiO_2$, $SiN_x$, $Al_2O_3$), but a type, a composition, etc., of the film can be arbitrarily selected. Other than the above, an organic insulating film, for example, can also be used, and the insulating film is not limited to the disclosure of the embodiments. Further, the material of the cap layer, the size and the number of ashing holes provided at the cap layer, the places where the ashing holes should be arranged, etc., can arbitrarily be changed according to specifications.

Also, application of the particle inspection chip is not necessarily limited to the semiconductor micro-analysis chip, and the particle inspection chip may be applied to a product with a tunnel flow channel formed by providing a cover over a fine groove formed on a glass substrate or a resin substrate. Further, the memory element is not limited to a fuse or a semiconductor memory, and may be any element as long as it changes its state according to use of the inspection chip and enables detection of the use by a change in electrical signals from the control module side. Further, in the above embodiments, cases of applying the inspection chip to inspection of viruses and bacteria have been described. However, the present embodiments are not limited to the above, and can be applied to inspection of various kinds of particles.

The particle inspection systems of the embodiments do not always have to be connected to a particle inspection chip. It is sufficient if the systems incorporate various circuits (a current-voltage conversion circuit, an analysis circuit, a detection circuit, a voltage driving circuit, etc.), and can be connected to a particle inspection chip needed for particle inspection.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A particle inspection system comprising:
   a voltage driving circuit which applies a driving voltage for particle inspection between two electrodes of a particle inspection chip, wherein the particle inspection chip detects a fine particle in a sample liquid based on a current flowing between the two electrodes and outputs a current signal indicative of the fine particle;
   a current-voltage conversion circuit which converts, into a voltage signal, the current signal output from the particle inspection chip when the driving voltage is applied;
   a detection circuit which detects, based on the voltage signal, whether the sample liquid is introduced into a detection region of the particle inspection chip; and an analysis circuit which analyzes the fine particle in the sample liquid based on the voltage signal, wherein the voltage driving circuit varies the driving voltage based on a detection result of the detection circuit, and wherein the voltage driving circuit applies a first driving voltage before the sample liquid is introduced into the detection region and applies a second driving voltage in response to the detection circuit detecting introduction of the sample liquid, wherein the first and second driving voltages are both nonzero and are different values from each other.

2. The system of claim 1, wherein the second driving voltage is higher than the first driving voltage.

3. The system of claim 2, wherein a time required for the driving voltage to shift from the first driving voltage to the second driving voltage is 10 μs or more.

4. The system of claim 1, wherein the particle inspection chip comprises:
a channel provided in a surface portion of a semiconductor substrate and permitting the sample liquid to pass therethrough, and
a micropore provided at part of the channel for passing therethrough the fine particle in the sample liquid.

5. The system of claim 1, wherein the particle inspection chip comprises:
a first channel provided in a surface portion of a semiconductor substrate and permitting the sample liquid to pass therethrough,
a second channel provided in a surface portion of the semiconductor substrate different from the surface portion of the first channel and permitting the sample liquid or an electrolyte to pass therethrough,
a contact portion at which part of the first channel is adjacent to or intersects part of the second channel with a partition interposed therebetween, and
a micropore provided in the partition for passing the fine particle therethrough.

6. The system of claim 1, wherein the particle inspection chip and a part of each circuit or each entire circuit are provided on a single semiconductor substrate.

7. A particle inspection system comprising:
a current driving circuit which applies a driving voltage for particle inspection between two electrodes of a particle inspection chip, to cause a constant current to flow in a detection region of the particle inspection chip, wherein the particle inspection chip detects a fine particle in a sample liquid and outputs a current signal indicative of the fine particle;
a current-voltage conversion circuit which converts, into a voltage signal, the current signal output from the particle inspection chip when the driving voltage is applied;
a detection circuit which detects whether the sample liquid is introduced into the detection region of the particle inspection chip, based on the voltage signal obtained by the current-voltage conversion circuit or the driving voltage applied by the current driving circuit; and
an analysis circuit which analyzes the fine particle in the sample liquid based on the voltage signal,
wherein the current driving circuit varies a value of the driving voltage to cause the current to vary in response to a detection result of the detection circuit.

8. The system of claim 7, wherein the current driving circuit applies a first driving voltage before the sample liquid is introduced into the detection region and applies a second driving voltage after the sample liquid is introduced into the detection region and the detection circuit detects the sample liquid,
wherein the first and second driving voltages are both nonzero, and
wherein the second driving voltage is higher than the first driving voltage.

9. The system of claim 8, wherein a time required for the driving voltage to shift from the first driving voltage to the second driving voltage is 10 μs or more.

10. The system of claim 7, wherein the particle inspection chip comprises:
a channel provided in a surface portion of a semiconductor substrate and permitting the sample liquid to pass therethrough, and
a micropore provided at part of the channel for passing therethrough the fine particle in the sample liquid.

11. The system of claim 7, wherein the particle inspection chip comprises:
a first channel provided in a surface portion of a semiconductor substrate and permitting the sample liquid to pass therethrough,
a second channel provided in a surface portion of the semiconductor substrate different from the surface portion of the first channel and permitting the sample liquid or an electrolyte to pass therethrough,
a contact portion at which part of the first channel is adjacent to or intersects part of the second channel with a partition interposed therebetween, and
a micropore provided in the partition for passing the fine particle therethrough.

12. The system of claim 7, wherein the particle inspection chip and a part of each circuit or each entire circuit are provided on a single semiconductor substrate.

13. A driving method for the particle inspection system recited in claim 1, the driving method comprising:
detecting, using the detection circuit, whether the sample liquid is introduced into the detection region, with the first driving voltage being applied between the two electrodes of the particle inspection chip;
applying the second driving voltage between the two electrodes of the particle inspection chip in response to introduction of the sample liquid into the detection region being detected; and
analyzing the fine particle in the sample liquid, using the analysis circuit and based on the voltage signal obtained by the current-voltage conversion circuit with the second driving voltage being applied.

14. The driving method of claim 13, wherein the second driving voltage is higher than the first driving voltage.

15. The driving method of claim 14, wherein a time required for the driving voltage to shift from the first driving voltage to the second driving voltage is 10 μs or more.

16. The driving method of claim 13, wherein the particle inspection chip comprises:
a channel provided in a surface portion of a semiconductor substrate and permitting the sample liquid to pass therethrough, and
a micropore provided at part of the channel for passing therethrough the fine particle in the sample liquid.

17. The driving method of claim 13, wherein the particle inspection chip comprises:
a first channel provided in a surface portion of a semiconductor substrate and permitting the sample liquid to pass therethrough,
a second channel provided in a surface portion of the semiconductor substrate different from the surface portion of the first channel and permitting the sample liquid or an electrolyte to pass therethrough, a contact portion at which part of the first channel is adjacent to or intersects part of the second channel with a partition interposed therebetween, and a micropore provided in the partition for passing the fine particle therethrough.

18. The driving method of claim 13, wherein the particle inspection chip and a part of each circuit or each entire circuit are provided on a single semiconductor substrate.

* * * * *